US009033981B2

(12) United States Patent
Olson et al.

(10) Patent No.: US 9,033,981 B2
(45) Date of Patent: *May 19, 2015

(54) VESSEL SEALER AND DIVIDER

(75) Inventors: Jessica E. Olson, Frederick, CO (US);
Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 393 days.

This patent is subject to a terminal disclaimer.

(21) Appl. No.: 13/491,853

(22) Filed: Jun. 8, 2012

(65) Prior Publication Data

US 2012/0310240 A1 Dec. 6, 2012

Related U.S. Application Data

(63) Continuation of application No. 12/331,643, filed on Dec. 10, 2008, now Pat. No. 8,197,479.

(51) Int. Cl.
*A61B 18/14* (2006.01)
*A61B 18/00* (2006.01)

(52) U.S. Cl.
CPC ... *A61B 18/1445* (2013.01); *A61B 2018/00083* (2013.01); *A61B 2018/00345* (2013.01); *A61B 2018/00404* (2013.01); *A61B 2018/00601* (2013.01); *A61B 2018/00619* (2013.01); *A61B 2018/0063* (2013.01); *A61B 2018/1412* (2013.01); *A61B 2018/1455* (2013.01)

(58) Field of Classification Search
CPC ............ A61B 18/1442; A61B 18/1445; A61B 18/1447
USPC ....................................................... 606/50–52
See application file for complete search history.

(56) References Cited

U.S. PATENT DOCUMENTS

D249,549 S   9/1978 Pike
D263,020 S   2/1982 Rau, III
(Continued)

FOREIGN PATENT DOCUMENTS

CN   201299462   9/2009
DE   2415263   10/1975
(Continued)

OTHER PUBLICATIONS

U.S. Appl. No. 08/926,869, filed Sep. 10, 1997, James G. Chandler.
(Continued)

*Primary Examiner* — Nicholas Lucchesi
*Assistant Examiner* — Melissa A Snyder

(57) ABSTRACT

An endoscopic bipolar forceps includes a housing and a shaft, the shaft having an end effector assembly which includes two jaw members for grasping tissue therebetween. Each jaw member is adapted to connect to an electrosurgical energy source, enabling them to effect a tissue seal to tissue held therebetween. A drive assembly is included within the housing for moving the jaw members. A movable handle is also included, and movement thereof actuates the drive assembly to move the jaw members relative to each other. A knife channel is included within the end effector configured to allow reciprocation of a knife blade within the knife channel. The knife blade includes a proximal edge adapted to engage a proximal edge of the end effector to impede translation of the knife blade when the jaw members are in an open configuration and the knife blade is retracted within the end effector assembly.

9 Claims, 28 Drawing Sheets

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| 6,041,679 A | 3/2000 | Slater et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,101,371 B2 | 9/2006 | Dycus et al. |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| 7,270,664 B2 | 9/2007 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,458,972 B2 | 12/2008 | Keppel |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,931,649 B2 | 4/2011 | Couture et al. |
| D649,249 S | 11/2011 | Guerra |
| D649,643 S | 11/2011 | Allen, IV et al. |
| D661,394 S | 6/2012 | Romero et al. |
| 2002/0188294 A1* | 12/2002 | Couture et al. ........ 606/51 |
| 2003/0018331 A1 | 1/2003 | Dycus et al. |
| 2003/0229344 A1 | 12/2003 | Dycus et al. |
| 2006/0084973 A1 | 4/2006 | Hushka |
| 2008/0195093 A1 | 8/2008 | Couture et al. |
| 2010/0063500 A1 | 3/2010 | Muszala |
| 2010/0179543 A1 | 7/2010 | Johnson et al. |
| 2010/0179545 A1 | 7/2010 | Twomey et al. |
| 2011/0082494 A1 | 4/2011 | Kerr et al. |
| 2012/0010614 A1 | 1/2012 | Couture |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1958583 | 8/2008 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |

(56) References Cited

FOREIGN PATENT DOCUMENTS

| WO | WO 02/45589 | 6/2002 |
|---|---|---|
| WO | WO 2004/073490 | 9/2004 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/488,093, filed Jun. 4, 2012, Kristin D. Johnson.
U.S. Appl. No. 13/491,853, filed Jun. 8, 2012, Jessica E. Olson.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2012, Joseph D. Bucciaglia.
U.S. Appl. No. 13/584,194, filed Aug. 13, 2012, Sean T. Dycus.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.

(56) References Cited

OTHER PUBLICATIONS

Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21:24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.

(56) References Cited

OTHER PUBLICATIONS

Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 168419.7 dated Oct. 20, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

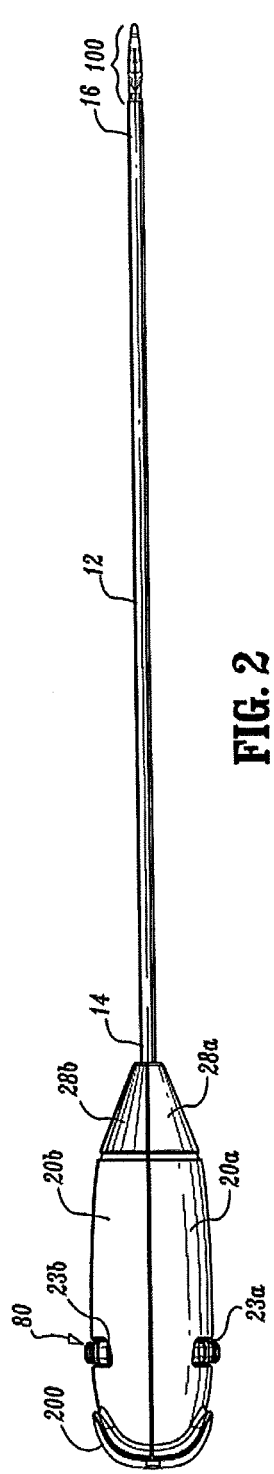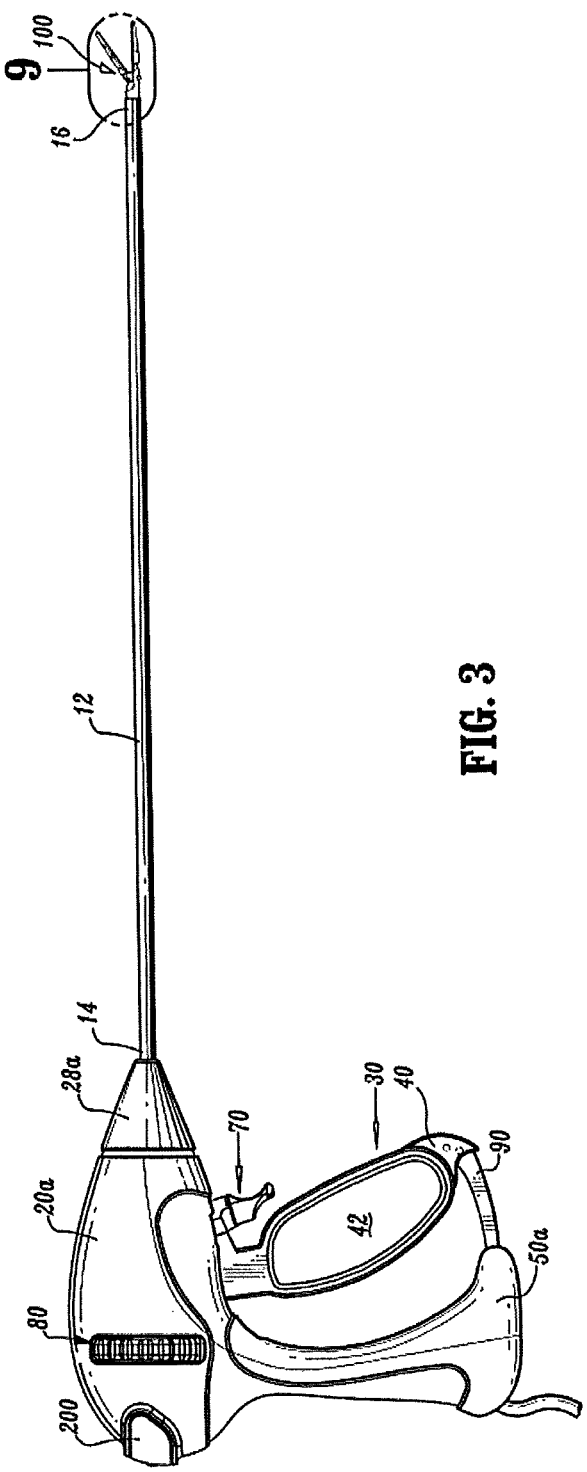
FIG. 2
FIG. 3

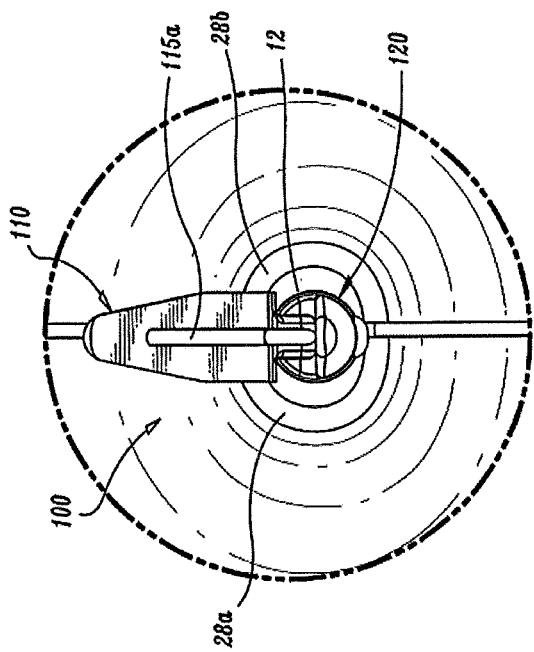
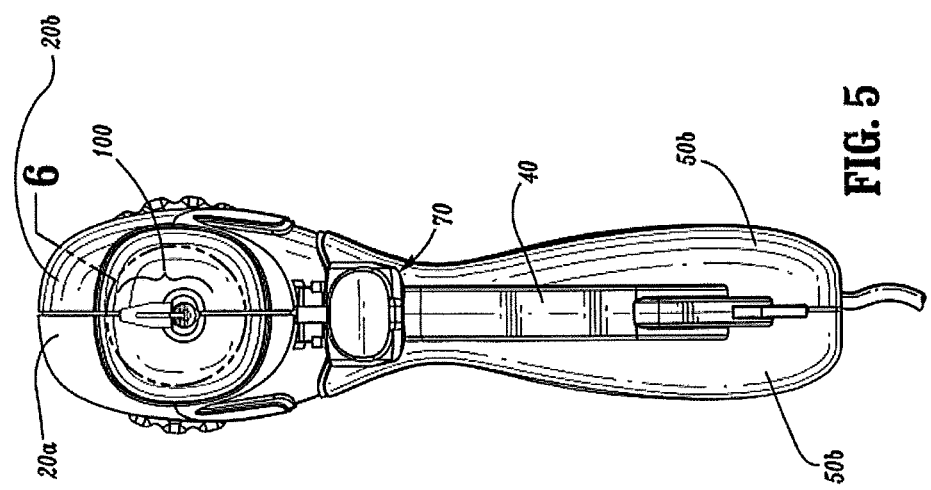
FIG. 6
FIG. 5

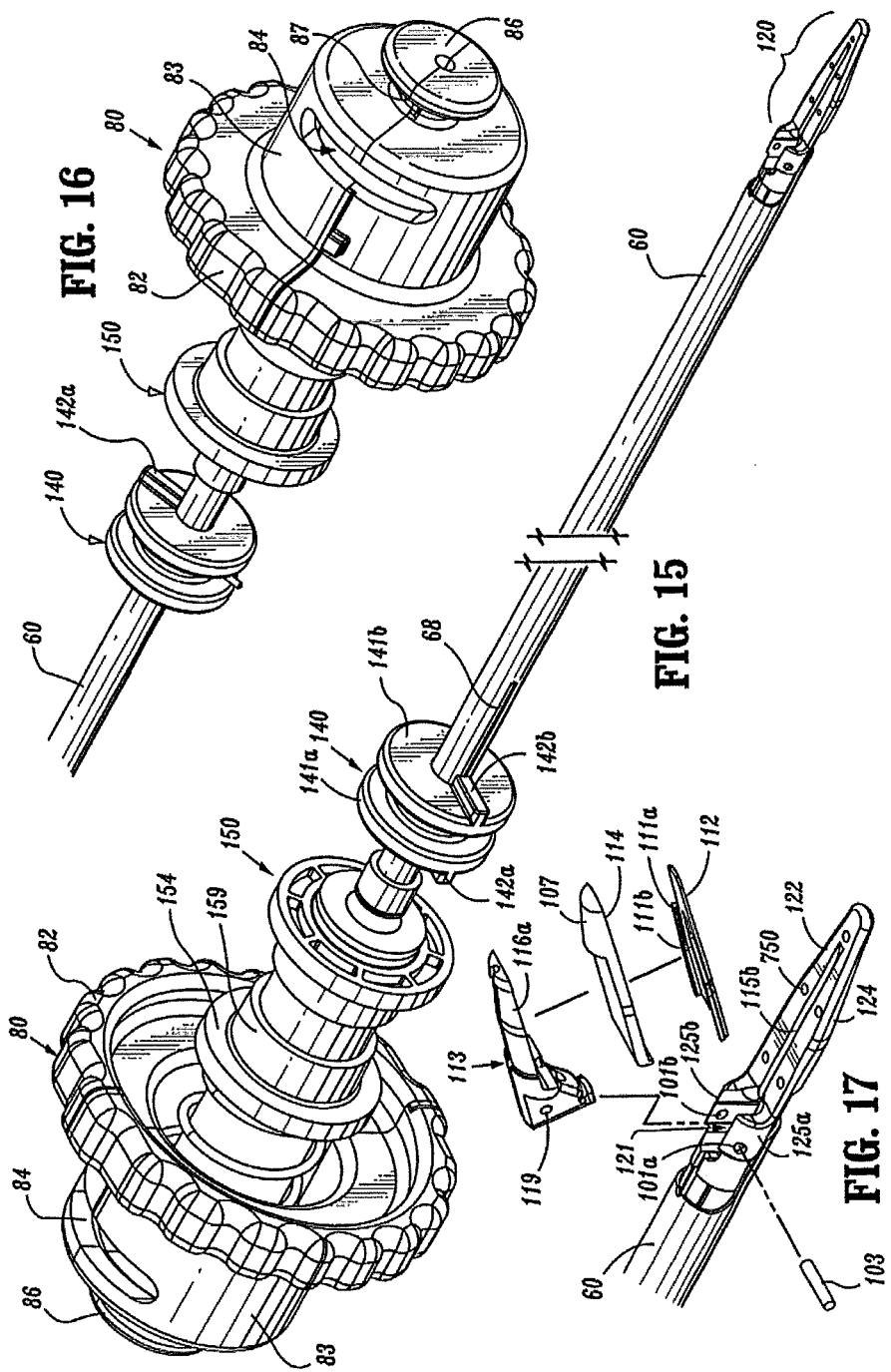

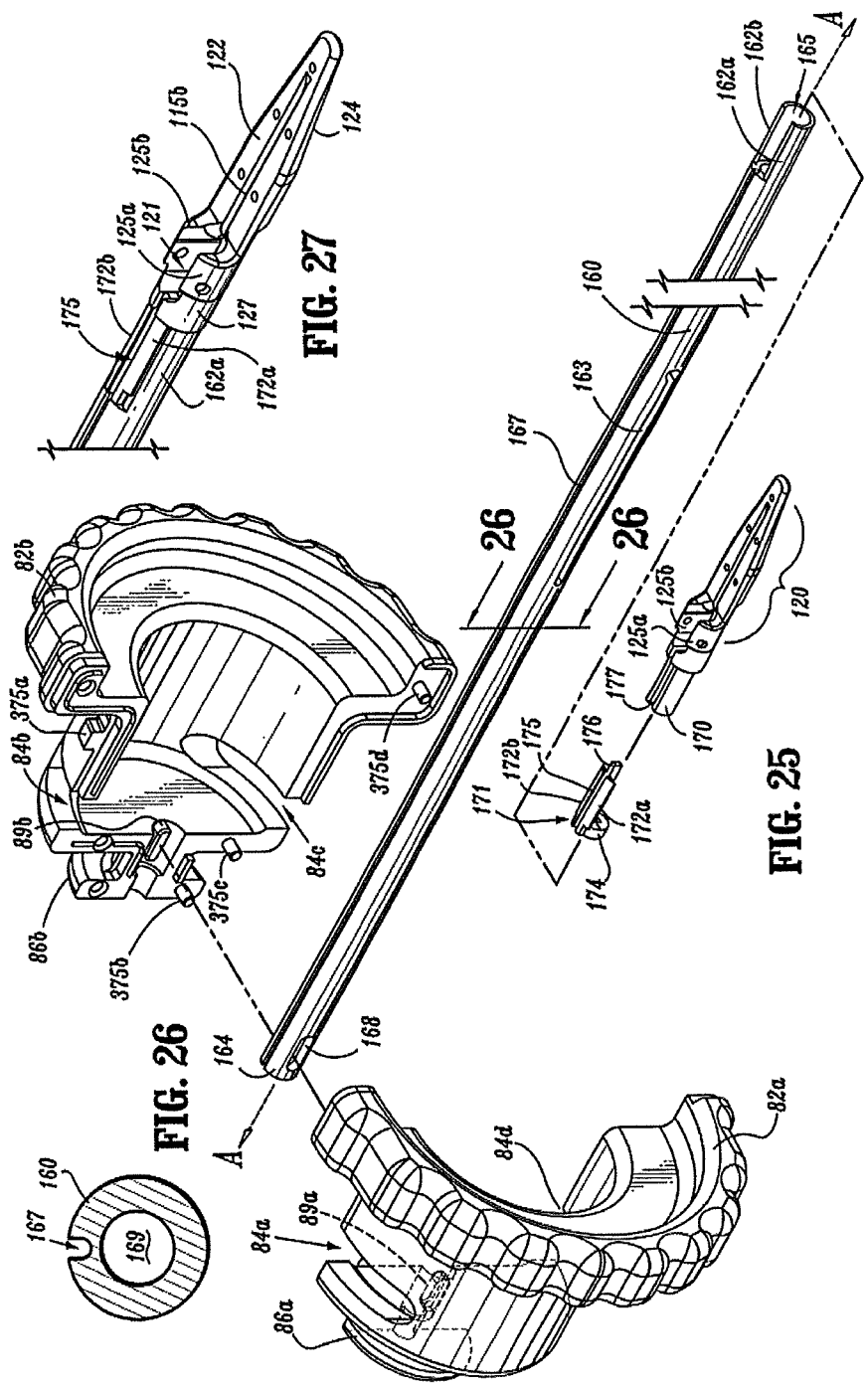

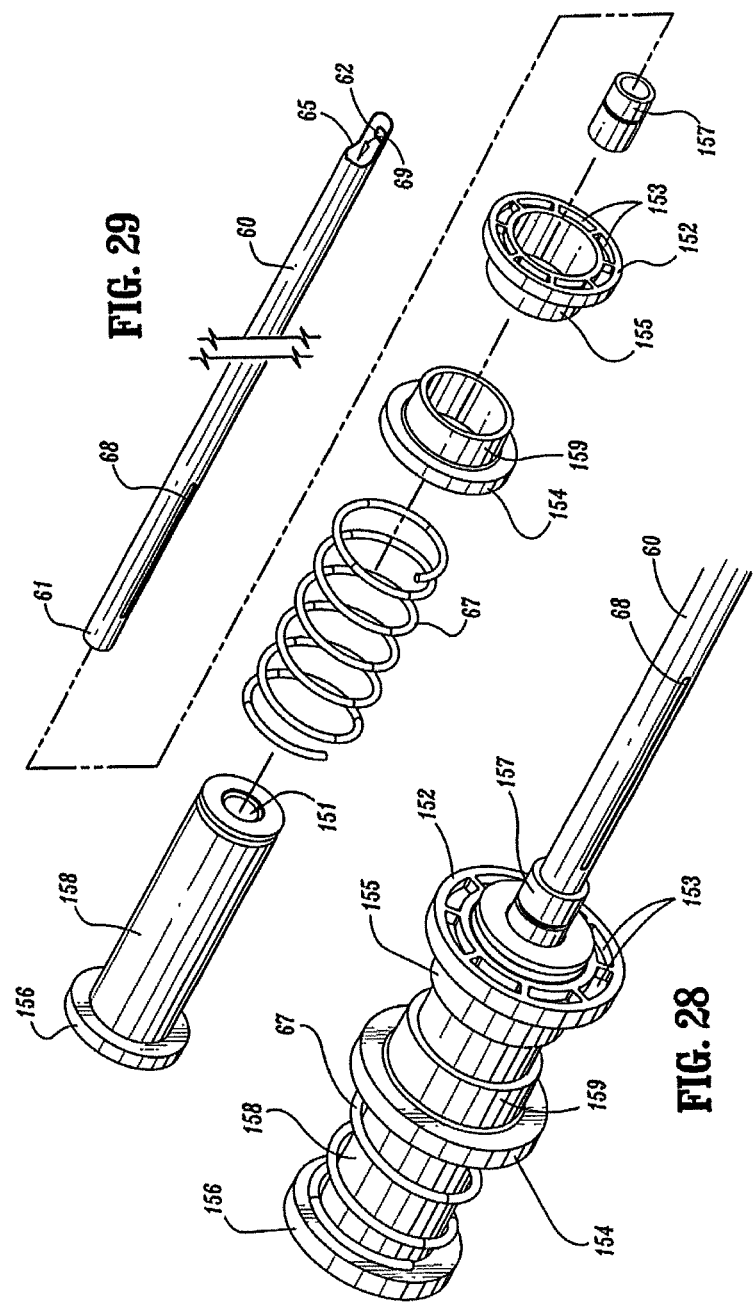

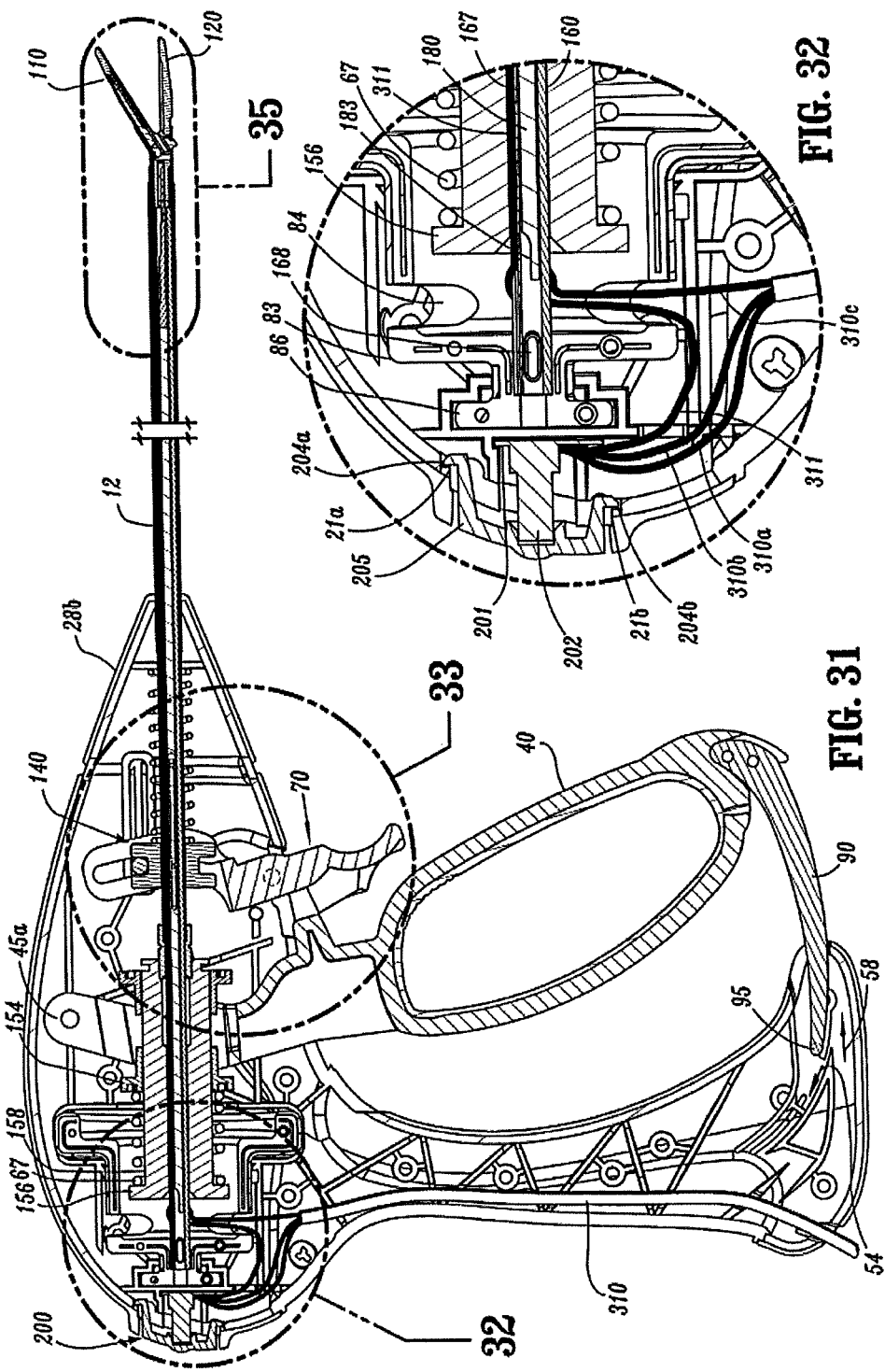

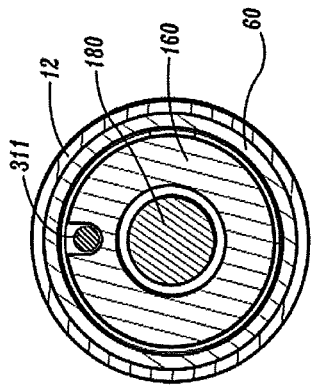
FIG. 34
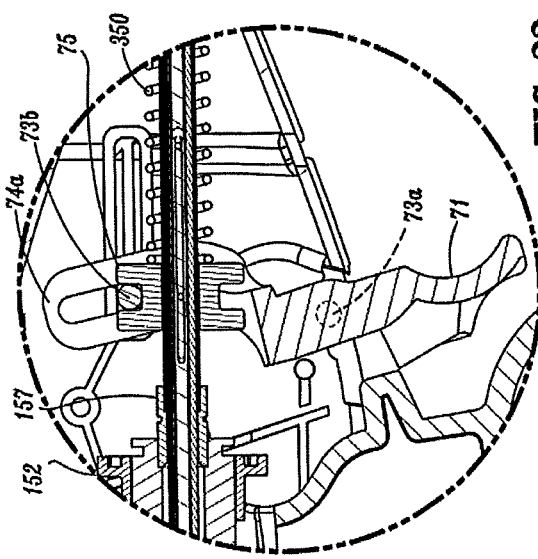
FIG. 33
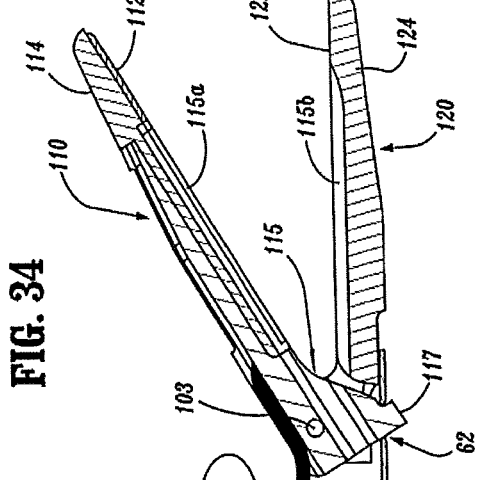
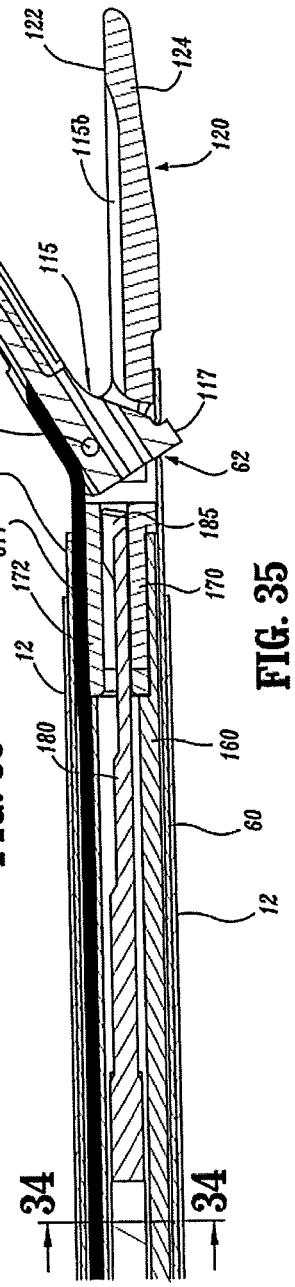
FIG. 35

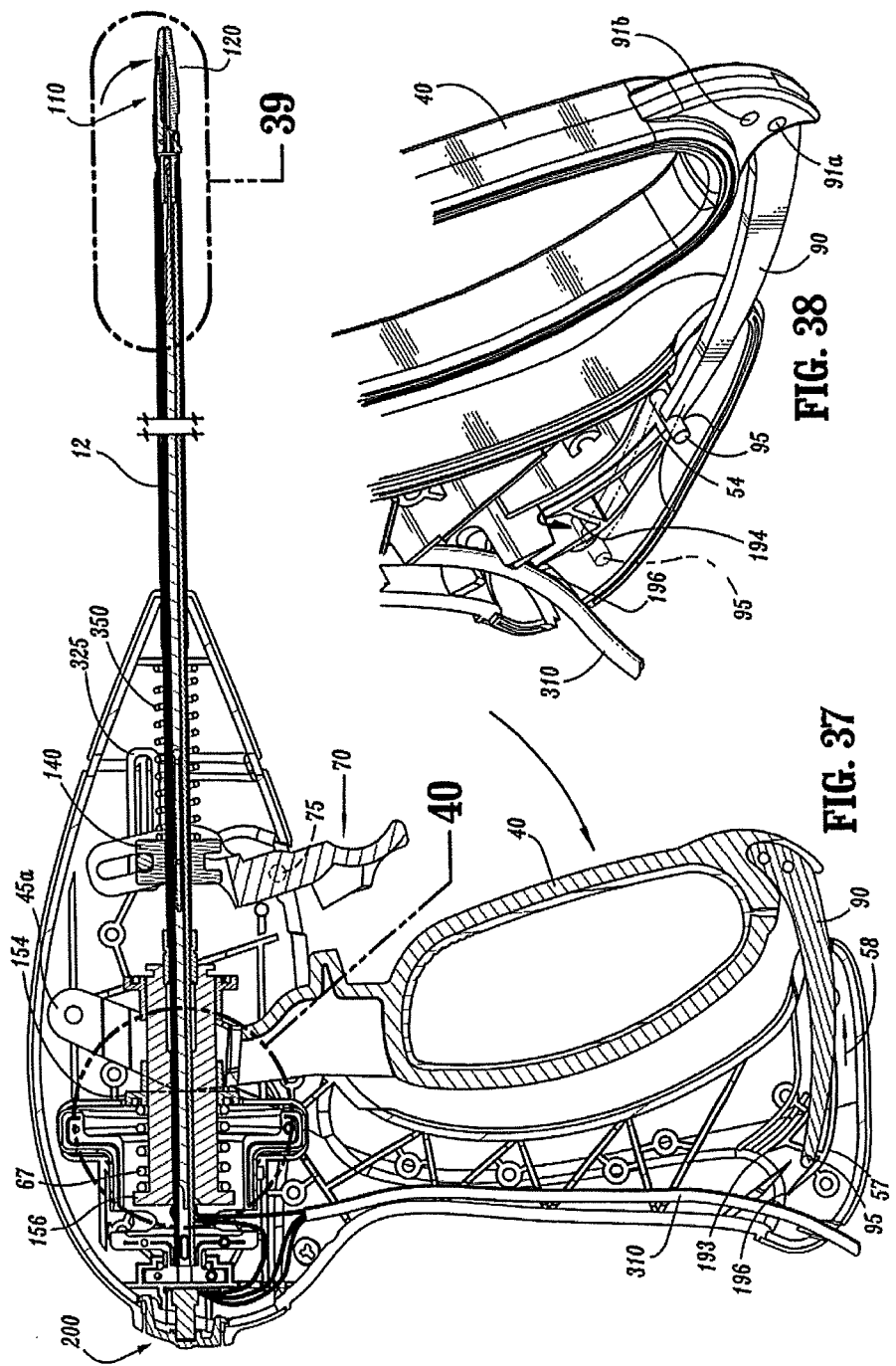

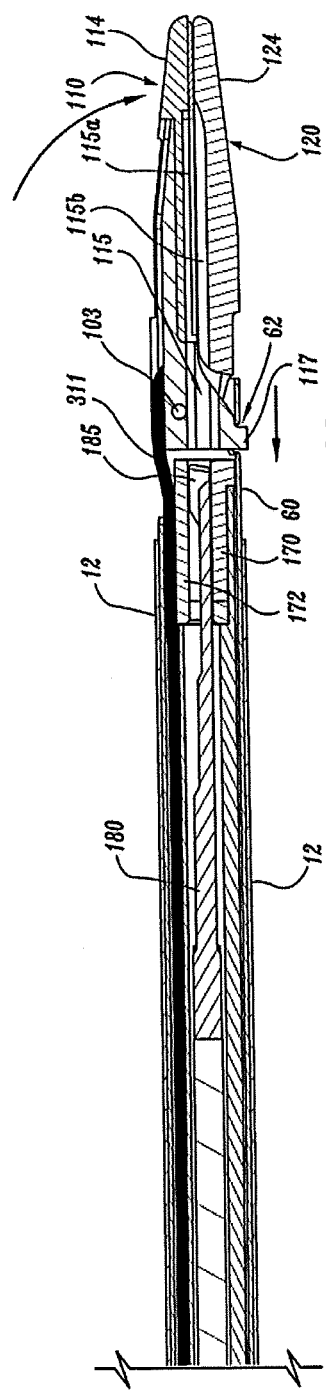
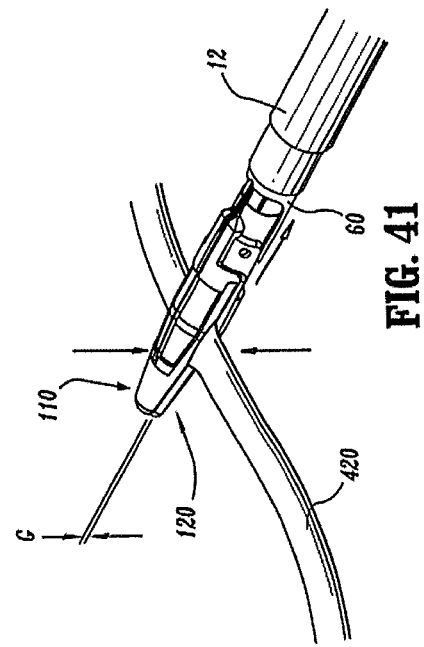
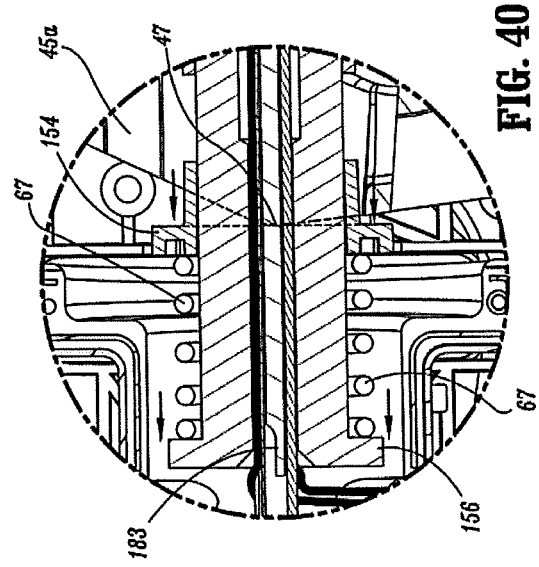
FIG. 39
FIG. 40
FIG. 41

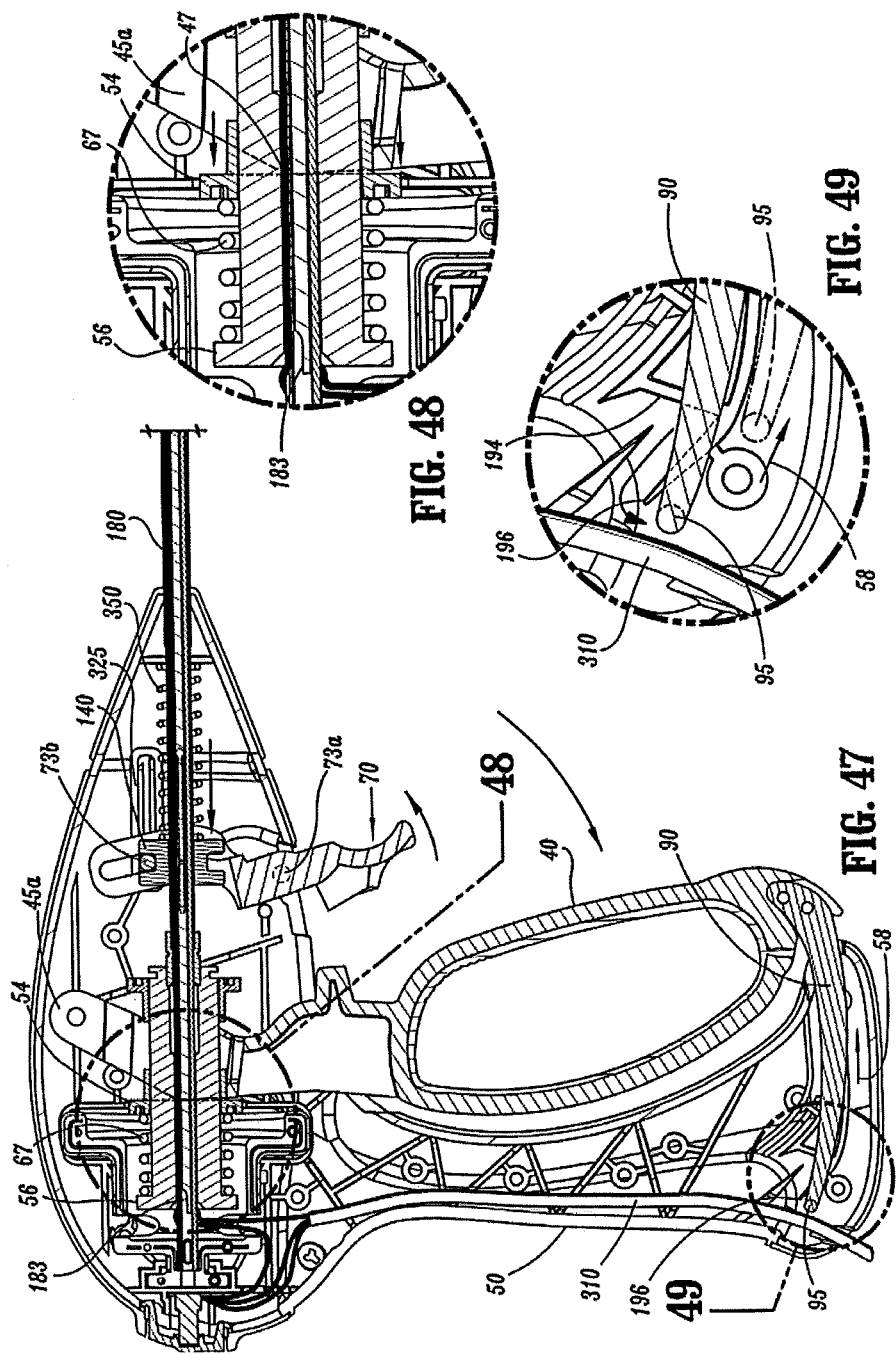

VESSEL SEALER AND DIVIDER

CROSS-REFERENCE TO RELATED APPLICATIONS

This application is a continuation of U.S. application Ser. No. 12/331,643 filed Dec. 10, 2008, and the disclosure of the above-identified application is hereby incorporated by reference in its entirety.

BACKGROUND

1. Technical Field

The present disclosure relates to an electrosurgical forceps and more particularly, the present disclosure relates to an endoscopic bipolar electrosurgical forceps for sealing and/or cutting tissue.

2. Background of Related Art

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic and/or laparoscopic instruments are inserted into the patient through a cannula, or a port, which has been made with a trocar. Typical sizes for cannulas range from three millimeters to twelve millimeters. Smaller cannulas are usually preferred, which, as can be appreciated, ultimately presents a design challenge to instrument manufacturers who attempt to find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

As mentioned above, in order to properly and effectively seal larger vessels or tissue, a greater closure force between opposing jaw members is required. It is known that a large closure force between the jaws typically requires a large moment about the pivot for each jaw. This presents a design challenge because the jaw members are typically affixed with pins which are positioned to have small moment arms with respect to the pivot of each jaw member. A large force, coupled with a small moment arm, is undesirable because the large forces may shear the pins. As a result, designers compensate for these large closure forces by either designing instruments with metal pins and/or by designing instruments which at least partially offload these closure forces to reduce the chances of mechanical failure. As can be appreciated, if metal pivot pins are employed, the metal pins should be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the tissue during compression and prior to activation. As a result thereof, providing an instrument which consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to uniformly, consistently and effectively seal the vessel. In other words, the success of the seal would greatly depend upon the ultimate skill of the surgeon rather than the efficiency of the instrument.

It has been found that the pressure range for assuring a consistent and effective seal is between about 3 kg/cm² to about 16 kg/cm² and, desirably, within a working range of 7 kg/cm² to 13 kg/cm². Manufacturing an instrument which is capable of providing a closure pressure within this working range has been shown to be effective for sealing arteries, tissues and other vascular bundles.

Various force-actuating assemblies have been developed in the past for providing the appropriate closure forces to effect vessel sealing. For example, one such actuating assembly has been developed by Valleylab, Inc. of Boulder, Colo., a division of Tyco Healthcare LP, for use with Valleylab's vessel sealing and dividing instrument commonly sold under the trademark LIGASURE ATLAS®. This assembly includes a four-bar mechanical linkage, a spring and a drive assembly which cooperate to consistently provide and maintain tissue pressures within the above working ranges. The LIGASURE ATLAS® is presently designed to fit through a 10 mm cannula and includes a bi-lateral jaw closure mechanism which is activated by a foot switch. A trigger assembly extends a knife distally to separate the tissue along the tissue seal. A rotating mechanism is associated with the distal end of the handle to allow a surgeon to selectively rotate the jaw members to facilitate grasping tissue. Co-pending U.S. application Ser. Nos. 11/348,072, 10/179,863 and 10/116,944, now issued U.S. Pat. Nos. 7,771,425, 7,101,371 and 7,083,618, respectively, and PCT Application Serial Nos. PCT/US01/01890 and PCT/US01/11340 describe in detail the operating features of the LIGASURE ATLAS® and various methods relating thereto.

SUMMARY

The present disclosure relates to an endoscopic bipolar forceps for use with various surgical procedures. The forceps includes a housing, a shaft, a drive assembly and a movable handle. The shaft includes an end effector assembly attached to a distal end thereof. The end effector assembly includes first and second jaw members movable from a first position in spaced relation to one another to at least a second position closer to one another. The jaw members are for grasping tissue therebetween. Each of the jaw members is adapted to connect to an electrosurgical energy source, thus enabling the jaw members to conduct energy through tissue held between the jaw members to create a tissue seal. At least one of the jaw members may be electrically or thermally insulated.

The forceps includes a drive assembly for moving the jaw members relative to one another from a first position wherein the jaw members are disposed in spaced relation relative to each other to a second position wherein the jaw members cooperate to grasp tissue therebetween. A movable handle is included which is rotatable about a pivot to actuate the drive assembly. The jaw members connect to a source of electrosurgical energy that carry electrical potentials to each respective jaw member such that the jaw members are capable of conducting bipolar energy through tissue held therebetween to affect a tissue seal.

In an embodiment, the end effector assembly includes a knife channel defined therein having a proximal and a distal end for reciprocation of a knife blade therethrough and a locking mechanism is adapted to impede advancement of the knife blade when the knife blade is in a retracted position and the jaw members are disposed in the first position.

The knife blade may have a notch defined therein wherein the notch has a proximal edge adapted to engage a proximal edge of the end effector assembly to impede distal translation of the knife blade when engaged. The knife blade may include a shaft having a notch defined therein and a distal end, the distal end including a height that is higher than the height of the shaft. The knife blade may be of a unitary construction.

The end effector assembly may include one movable jaw member and one stationary jaw member wherein the distal end of the knife blade is dimensioned to ride within the knife channel of the rigid jaw.

An angle defined by the distal end of the knife blade and a perpendicular line to a surface to be cut may be selected from the group consisting of positive, negative, and neutral angles.

In a further embodiment, at least one of the jaw members may be made from a stiffer material, thereby reducing the flexibility of the jaw member, and improving seal performance. The distal end of the end effector assembly may have a variety of shapes including a blunt end. In still another embodiment, at least one of the jaw members has a texturized surface for facilitating grasping and retaining of tissue. Stop members may be included on at least one of the jaw members to create a gap between the jaw members when they are disposed in the second position. The jaw members may also be coated with a nonstick material.

BRIEF DESCRIPTION OF THE DRAWINGS

Various embodiments of the subject instrument are described herein with reference to the drawings wherein:

FIG. 2 is a top view of the forceps of FIG. 1;

FIG. 3 is a side view of the forceps of FIG. 1;

FIG. 5 is a front view of the forceps of FIG. 1;

FIG. 6 is an enlarged view of the indicated area of detail of FIG. 5 showing an enhanced view of the end effector assembly detailing a pair of opposing jaw members;

FIG. 15 is a perspective view of a rotating assembly, drive assembly, knife assembly and lower jaw member according to the present disclosure;

FIG. 16 is a rear, perspective view of the rotating assembly, drive assembly and knife assembly;

FIG. 17 is an enlarged, top, perspective view of the end effector assembly with parts separated;

FIG. 25 is an enlarged, perspective view of the rotating assembly and lower jaw member with parts separated;

FIG. 26 is a cross section of the area indicated in detail in FIG. 25;

FIG. 27 is a greatly-enlarged, perspective view of the lower jaw member;

FIG. 28 is an enlarged, perspective view of the drive assembly;

FIG. 29 is an enlarged perspective view of the drive assembly of FIG. 28 with parts separated;

FIG. 31 is a cross-section of the housing with the end effector shown in open configuration and showing the internal, electrical routing of an electrosurgical cable and electrical leads;

FIG. 32 is a greatly-enlarged view of the indicated area of detail of FIG. 31;

FIG. 33 is a greatly-enlarged view of the indicated area of detail of FIG. 31;

FIG. 34 is a greatly-enlarged, cross section of the shaft taken along line 34-34;

FIG. 35 is a side, cross section of the shaft and end effector assembly;

FIG. 37 is a side, cross section of the housing showing the moving components of the drive assembly during actuation;

FIG. 38 is a greatly-enlarged, perspective view of a handle locking mechanism for use with the drive assembly;

FIG. 39 is a greatly-enlarged view of the indicated area of detail in FIG. 37;

FIG. 40 is a greatly-enlarged view of the indicated area of detail in FIG. 37;

FIG. 41 is an enlarged, rear, perspective view of an end effectors shown grasping tissue;

FIG. 47 is a side, cross section of the housing showing the release of the knife assembly and release of the drive assembly to open the jaw members and release the tissue;

FIG. 48 is a greatly-enlarged view of the indicated area of detail in FIG. 47;

FIG. 49 is a greatly-enlarged view of the indicated area of detail in FIG. 47;

DETAILED DESCRIPTION

The present disclosure describes an endoscopic bipolar forceps 10 including multiple assemblies, i.e., a handle assembly, a rotating assembly, a trigger assembly, and an end effector assembly. It will be understood that other assemblies may be substituted for those described herein.

In particular, two embodiments of an end effector assembly, 100 and 500, are described herein. It will be understood that each end effector assembly, 100 and 500, may be substituted for one another without modification to the forceps 10 in any other way.

Figure 1:
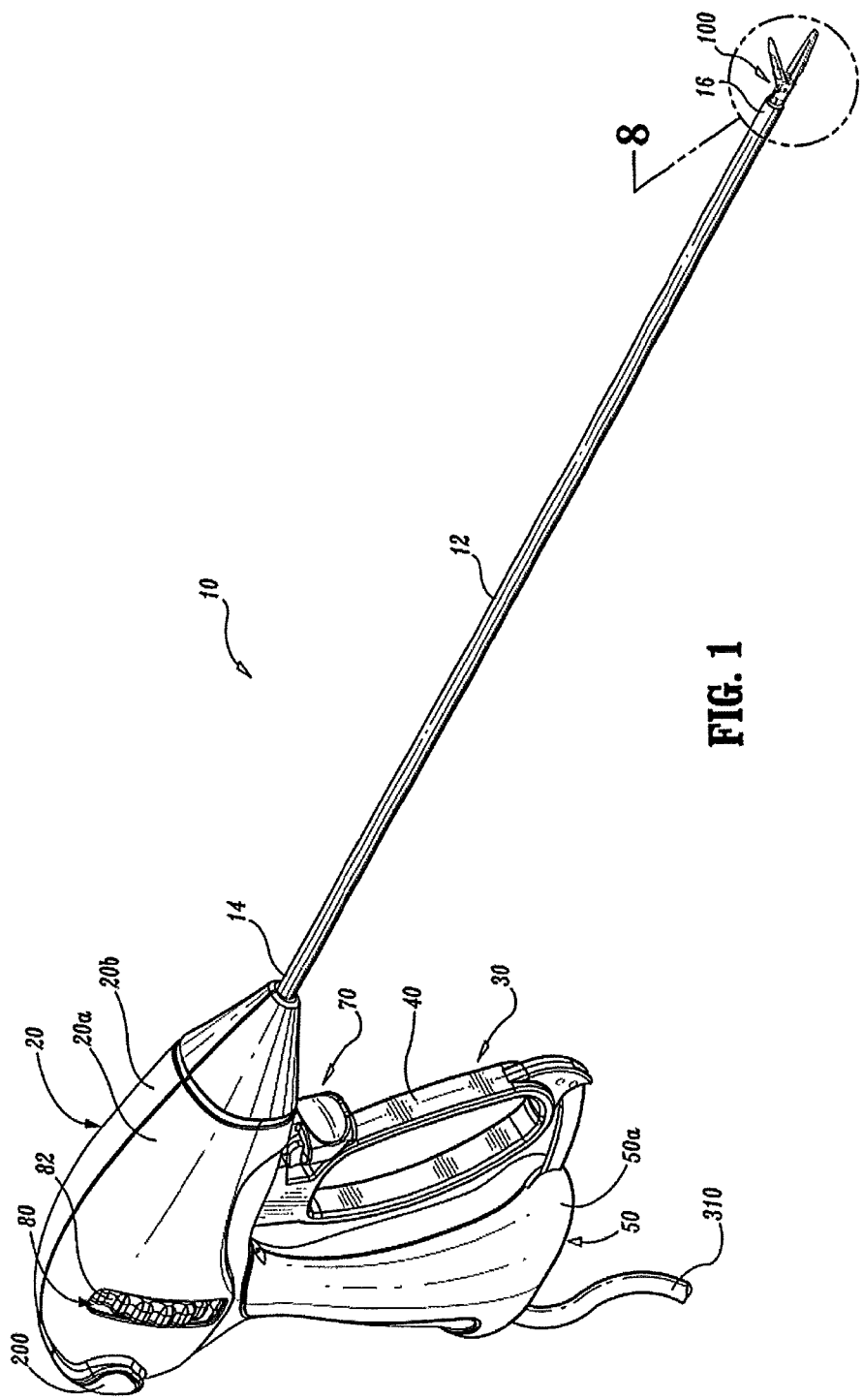
FIG. 1 is a perspective view of an endoscopic bipolar forceps showing a housing, a shaft and an end effector assembly according to the present disclosure.
Figure 36:
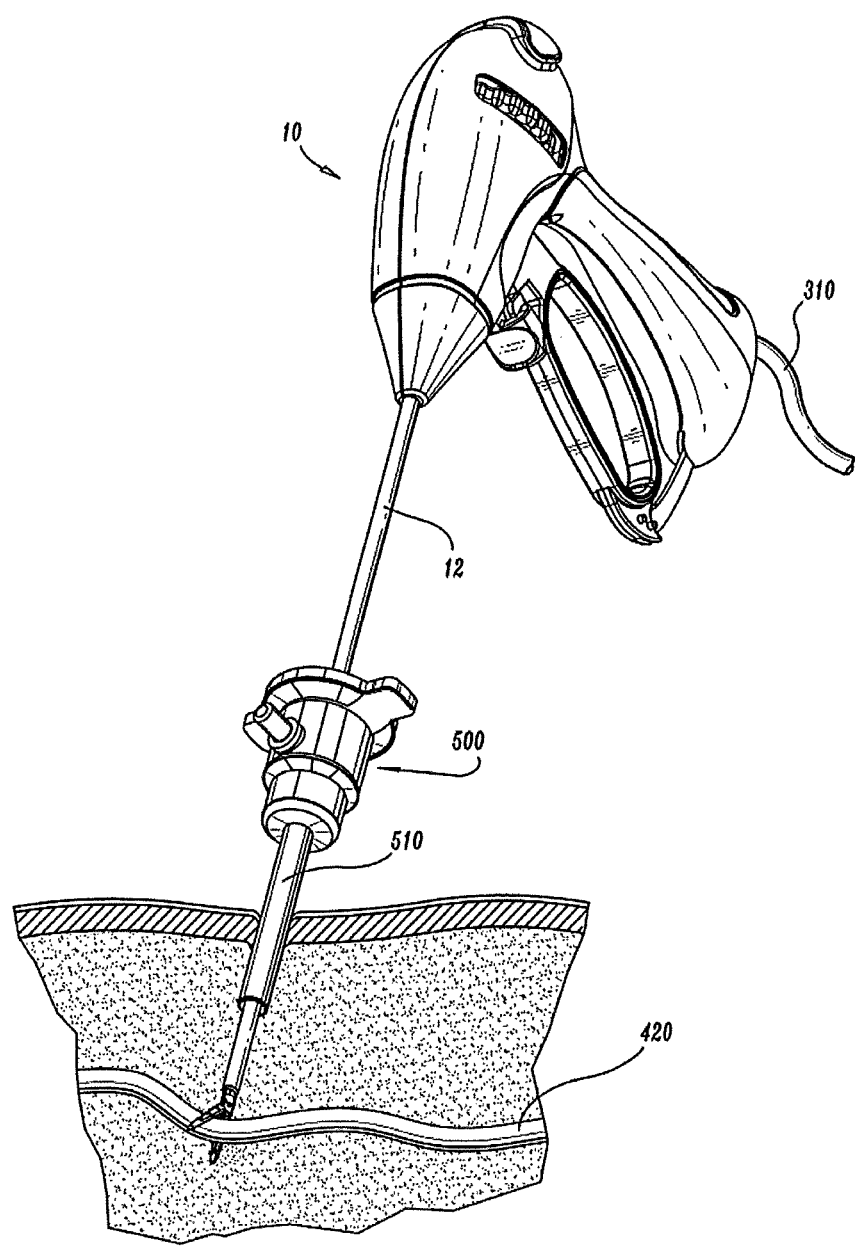
FIG. 36 is a perspective view showing the forceps of the present disclosure being utilized with a 5 mm cannula.

Turning now to FIGS. 1-3, one embodiment of an endoscopic bipolar forceps 10 is shown for use with various surgical procedures and generally includes a housing 20, a handle assembly 30, a rotating assembly 80, a trigger assembly 70 and an end effector assembly 100 which mutually cooperate to grasp, seal and divide tubular vessels and vascular tissue 420 (FIG. 36). Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

Forceps 10 includes a shaft 12 which has a distal end 16 dimensioned to mechanically engage either the end effector assembly 100 or the end effector assembly 500 and a proximal end 14 which mechanically engages the housing 20. Details of how the shaft 12 connects to the end effector assembly 100 or alternatively 500 are described in more detail below with respect to FIG. 25, shown with the end effector assembly 100. The proximal end 14 of shaft 12 is received within the housing 20 and the connections relating thereto are described in detail below with respect to FIGS. 13 and 14. In the drawings and in the descriptions which follow, the term "proximal," as is traditional, will refer to the end of the forceps 10 which is closer to the user, while the term "distal" will refer to the end which is farther from the user.

As best seen in FIG. 1, forceps 10 also includes an electrosurgical cable 310 which connects the forceps 10 to a source of electrosurgical energy, e.g., a generator (not shown). It is contemplated that generators such as those sold by Valleylab—a division of Tyco Healthcare LP, located in Boulder Colo. are used as a source of electrosurgical energy, e.g., FORCE EZ™ Electrosurgical Generator, FORCE FX™ Electrosurgical Generator, FORCE 1C™, FORCE 2™ Generator, SurgiStat™ II. One such system is described in commonly-owned U.S. Pat. No. 6,033,399 entitled "ELECTROSURGICAL GENERATOR WITH ADAPTIVE POWER CONTROL". Other systems have been described in commonly-owned U.S. Pat. No. 6,187,003 entitled "BIPOLAR ELECTROSURGICAL INSTRUMENT FOR SEALING VESSELS".

In one embodiment, the generator includes various safety and performance features including isolated output, independent activation of accessories. It is envisioned that the electrosurgical generator includes Valleylab's Instant Response™ technology features which provides an advanced feedback system to sense changes in tissue 200 times per second and adjust voltage and current to maintain appropriate power. The Instant Response™ technology is believed to provide one or more of the following benefits to surgical procedure:

Consistent clinical effect through all tissue types;
Reduced thermal spread and risk of collateral tissue damage;
Less need to "turn up the generator"; and
Designed for the minimally invasive environment.

Figure 30:
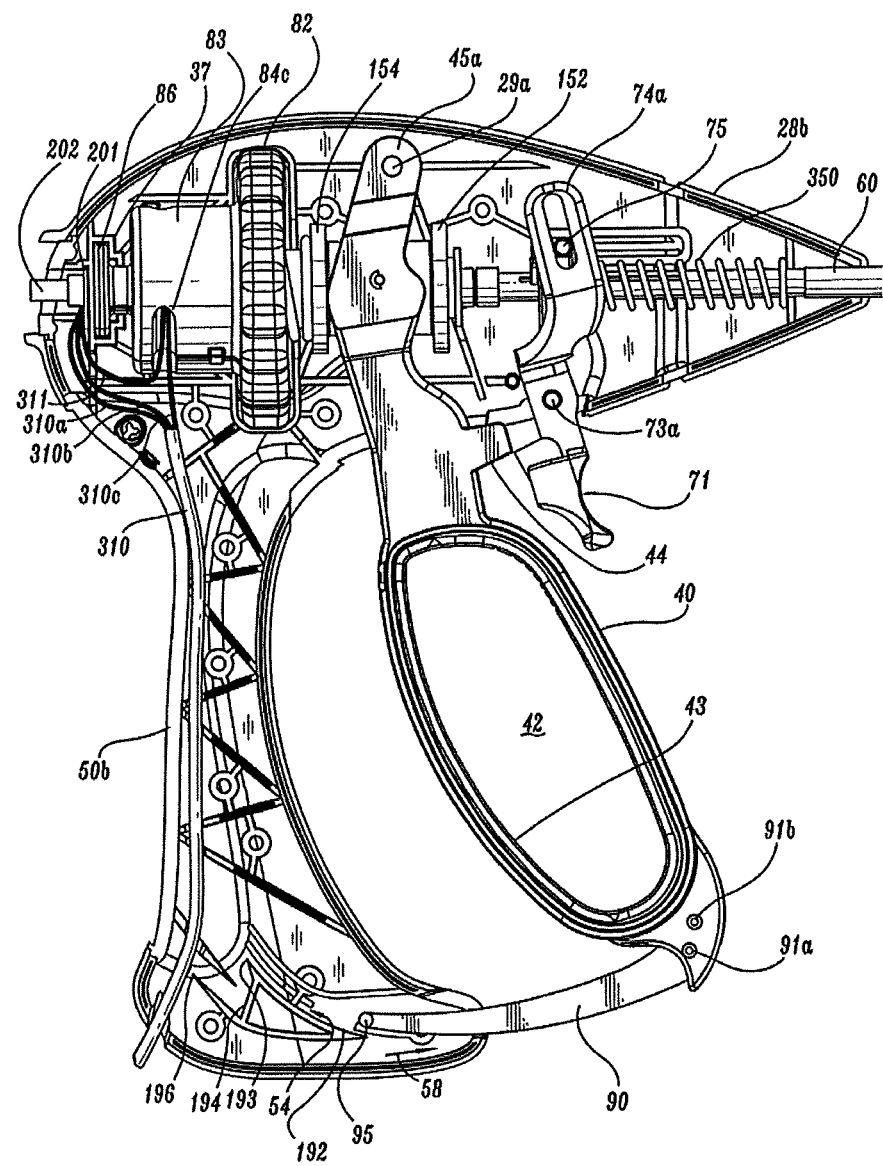
FIG. 30 is an internal, side view of the housing showing the inner-working components thereof.

Cable 310 is internally divided into cable lead 310a, 310b and 310c which each transmit electrosurgical energy through their respective feed paths through the forceps 10 to the end effector assembly 100 as explained in more detail below with respect to FIGS. 14 and 30.

Cable 310 is internally divided into cable lead 310a, 310b and 310c which each transmit electrosurgical energy through their respective feed paths through the forceps 10 to the end effector assembly 100 as explained in more detail below with respect to FIGS. 14 and 30.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. In one embodiment, rotating assembly 80 is integrally associated with the housing 20 and is rotatable approximately 180 degrees in either direction about a longitudinal axis "A" (See FIG. 4). Details of the rotating assembly 80 are described in more detail with respect to FIGS. 13, 14, 15 and 16.

Figure 13:
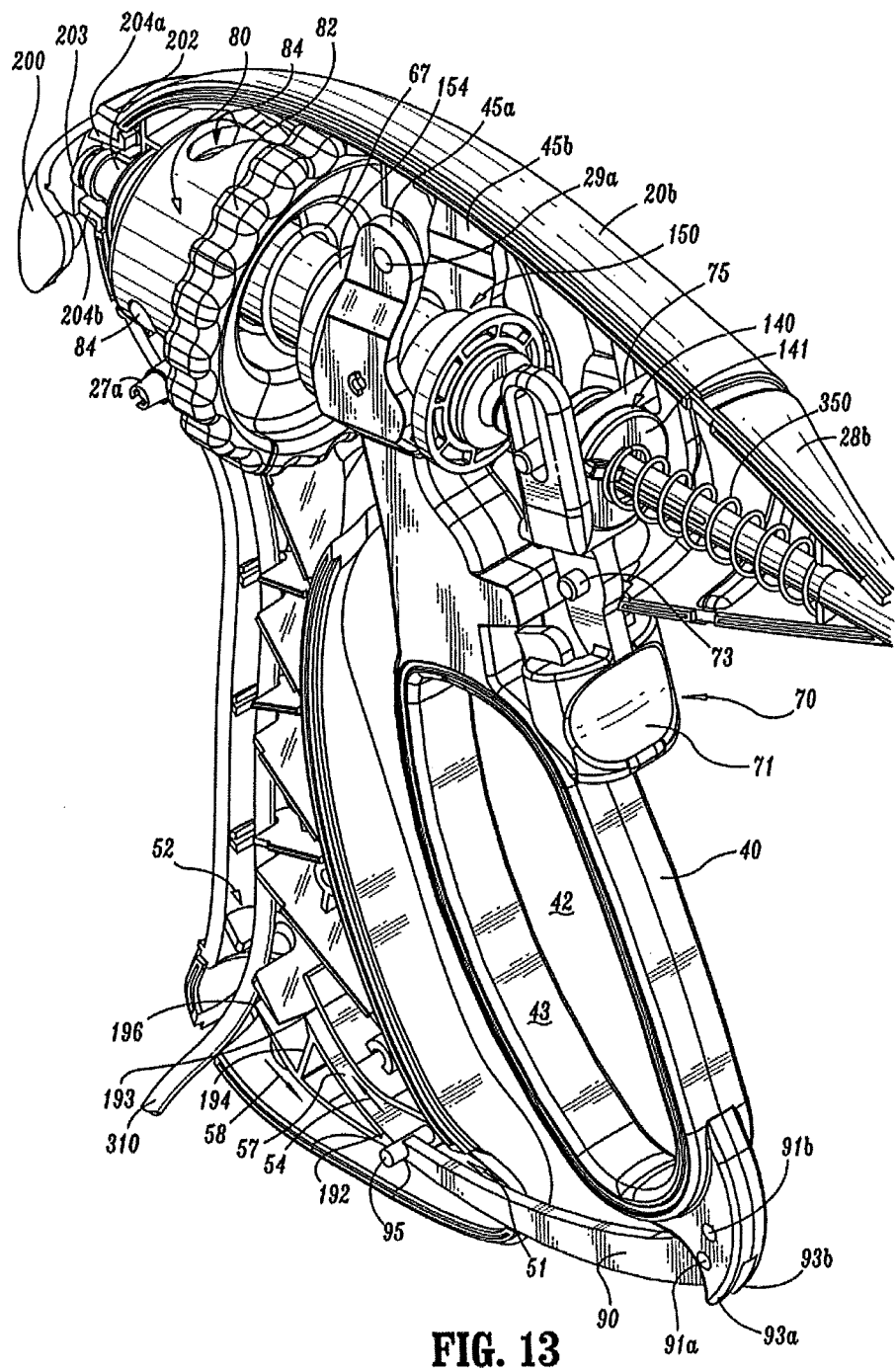
FIG. 13 is an enlarged, perspective view of the housing showing the internal working components thereof.
Figure 14:
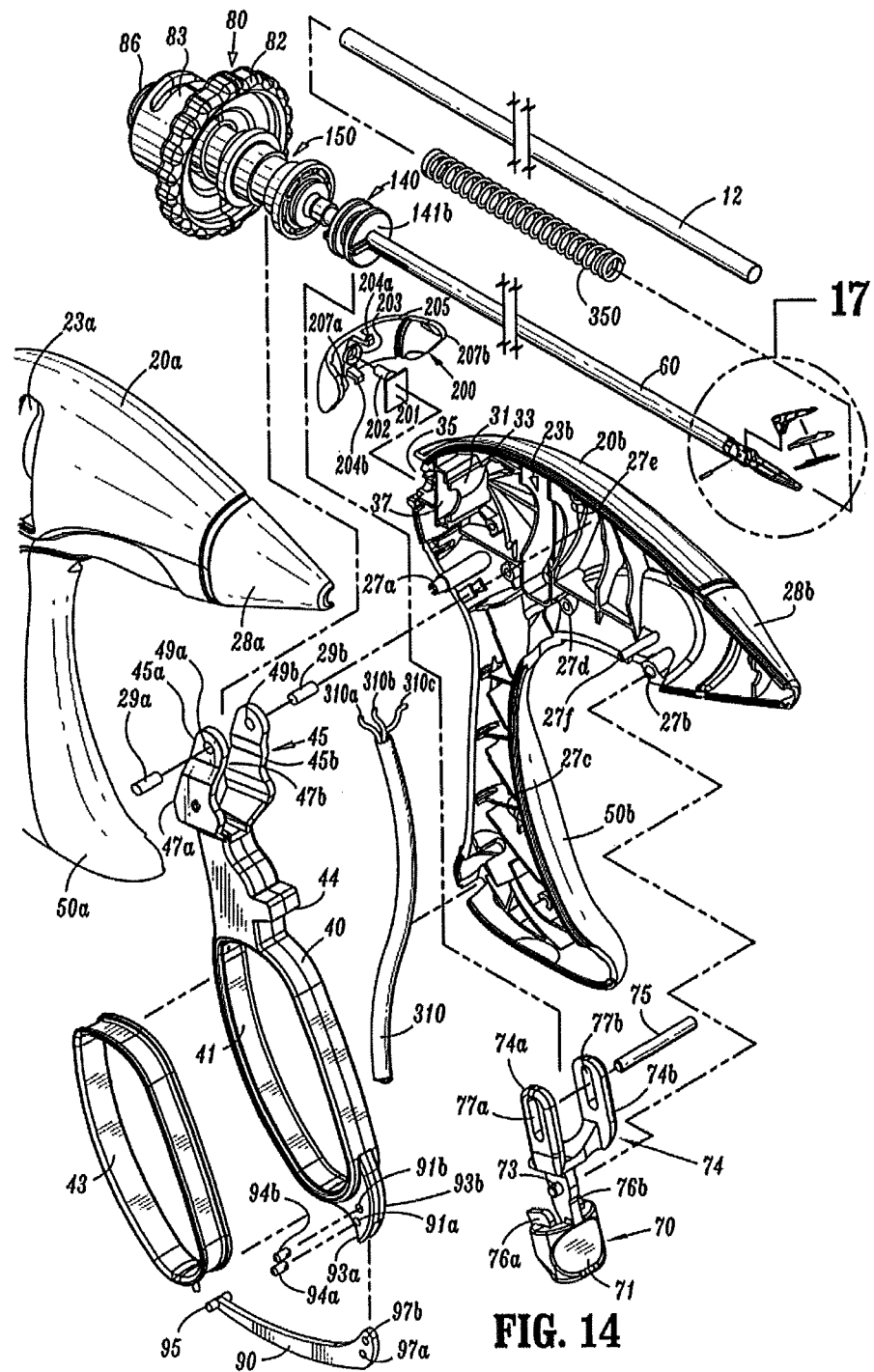
FIG. 14 is top, perspective view of the housing of FIG. 13 with parts separated.

As best seen in FIGS. 2, 13 and 14, housing 20 is formed from two (2) housing halves 20a and 20b which each include a plurality of interfaces 27a-27f which are dimensioned to mechanically align and engage one another to form housing 20 and enclose the internal working components of forceps 10. As can be appreciated, fixed handle 50 which, as mentioned above, is integrally associated with housing 20, takes shape upon the assembly of the housing halves 20a and 20b.

It is envisioned that a plurality of additional interfaces (not shown) may disposed at various points around the periphery of housing halves 20a and 20b for ultrasonic welding purposes, e.g., energy direction/deflection points. It is also contemplated that housing halves 20a and 20b (as well as the other components described below) may be assembled together in any fashion known in the art. For example, alignment pins, snap-like interfaces, tongue and groove interfaces, locking tabs, adhesive ports, etc. may all be utilized either alone or in combination for assembly purposes.

Rotating assembly 80 includes two halves 82a and 82b which, when assembled, form the rotating assembly 80 which, in turn, houses the drive assembly 150 and the knife assembly 140 (See FIGS. 13, 14 and 25). Half 82b includes a series of detents/flanges 375a, 375b, 375c and 375d (FIG. 25) which are dimensioned to engage a pair of corresponding sockets or other mechanical interfaces (not shown) disposed within rotating half 82a. In one embodiment, movable handle 40 and trigger assembly 70 are of unitary construction and are operatively connected to the housing 20 and the fixed handle 50 during the assembly process.

As previously discussed, different embodiments of assemblies may be substituted for those described herein and configured for use with forceps 10. Described immediately below is the end effector assembly 100. However, it will be understood that the end effector assembly 500 and the end effector assembly 100 may be substituted for one another and coupled with the forceps 10.

The end effector assembly 100 may be attached at the distal end 16 of shaft 12 and includes a pair of opposing jaw members 110 and 120. Movable handle 40 of handle assembly 30 is ultimately connected to a drive assembly 150 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue 420 (FIG. 36) therebetween.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

Turning now to the more detailed features of the present disclosure as described with respect to FIGS. 1-14, movable handle 40 includes a finger loop 41 which has an aperture 42 defined therethrough which enables a user to grasp and move the handle 40 relative to the fixed handle 50. Handle 40 also includes an ergonomically-enhanced gripping element 43 disposed along the inner peripheral edge of aperture 42 which is designed to facilitate gripping of the movable handle 40 during activation. It is envisioned that gripping element 43 may include one or more protuberances, scallops and/or ribs to enhance gripping. As best seen in FIG. 14, movable handle 40 is selectively movable about a pair of pivot pins 29a and 29b from a first position relative to fixed handle 50 to a second position in closer proximity to the fixed handle 50 which, as explained below, imparts movement of the jaw members 110 and 120 relative to one another. The movable handle include a clevis 45 which forms a pair of upper flanges 45a and 45b each having an aperture 49a and 49b, respectively, at an upper end thereof for receiving the pivot pins 29a and 29b therethrough and mounting the upper end of the handle 40 to the housing 20. In turn, each pin 29a and 29b mounts to a respective housing half 20a and 20b.

Each upper flange 45a and 45b also includes a force-actuating flange or drive flange 47a and 47b, respectively, which are aligned along longitudinal axis "A" and which abut the drive assembly 150 such that pivotal movement of the handle 40 forces actuating flange against the drive assembly 150 which, in turn, closes the jaw members 110 and 120. For the purposes herein, 47a and 47b which act simultaneously on the drive assembly are referred to as "driving flange 47". A more detailed explanation of the inter-cooperating components of the handle assembly 30 and the drive assembly 150 is discussed below.

As best seen in FIG. 14, the lower end of the movable handle 40 includes a flange 90 which can be mounted to the movable handle 40 by pins 94a and 94b which engage a corresponding pair of apertures 91a and 91b disposed within the lower portion of handle 40 and apertures 97a and 97b disposed within flange 90, respectively. Other methods of engagement are also contemplated, snap-lock, spring tab, etc. Flange 90 also includes a t-shaped distal end 95 which rides within a predefined channel 51 disposed within fixed handle 50 to lock the movable handle 40 relative to the fixed handle 50. Additional features with respect to the t-shaped end 95 are explained below in the detailed discussion of the operational features of the forceps 10.

Movable handle 40 is designed to provide a distinct mechanical advantage over conventional handle assemblies due to the unique position of the pivot pins 29a and 29b (i.e., pivot point) relative to the longitudinal axis "A" of the shaft 12 and the disposition of the driving flange 47 along longitudinal axis "A". In other words, it is envisioned that by positioning the pivot pins 29a and 29b above the driving flange 47, the user gains lever-like mechanical advantage to actuate the jaw members 110 and 120 enabling the user to close the jaw members 110 and 120 with lesser force while still generating the required forces necessary to effect a proper and effective tissue seal. It is also envisioned that the unilateral design of the end effector assembly 100 will also increase mechanical advantage as explained in more detail below.

As shown best in FIGS. 6-12, the end effector assembly 100 includes opposing jaw members 110 and 120 which cooperate to effectively grasp tissue 420 for sealing purposes. The end effector assembly 100 is designed as a unilateral assembly, i.e., jaw member 120 is fixed relative to the shaft 12 and jaw member 110 pivots about a pivot pin 103 to grasp tissue 420.

Figure 12:
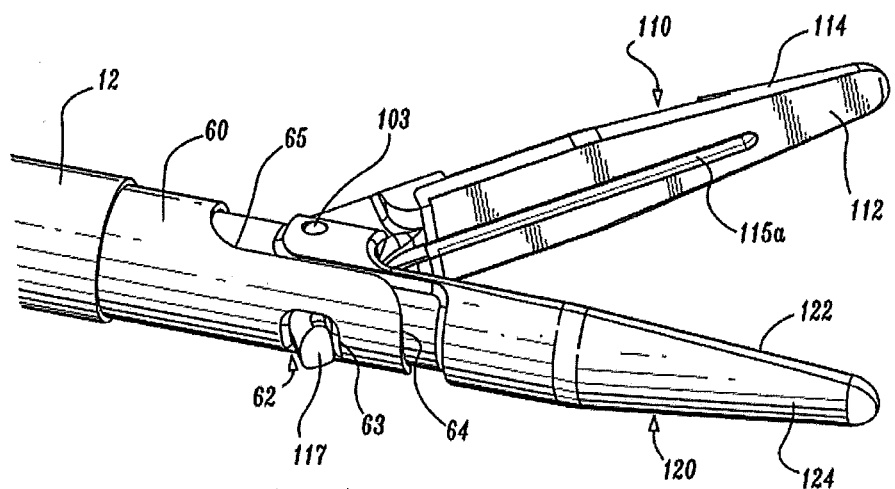
FIG. 12 is a full perspective view of the end effector assembly of FIG. 11.

More particularly, the unilateral end effector assembly 100 includes one stationary or fixed jaw member 120 mounted in fixed relation to the shaft 12 and pivoting jaw member 110 mounted about a pivot pin 103 attached to the stationary jaw member 120. A reciprocating sleeve 60 is slidingly disposed within the shaft 12 and is remotely operable by the drive assembly 150. The pivoting jaw member 110 includes a detent or protrusion 117 which extends from jaw member 110 through an aperture 62 disposed within the reciprocating sleeve 60 (FIG. 12). The pivoting jaw member 110 is actuated by sliding the sleeve 60 axially within the shaft 12 such that a distal end 63 of the aperture 62 abuts against the detent 117 on the pivoting jaw member 110 (See FIGS. 11 and 12). Pulling the sleeve 60 proximally closes the jaw members 110 and 120 about tissue 420 grasped therebetween and pushing the sleeve 60 distally opens the jaw members 110 and 120 for grasping purposes.

Figure 8:
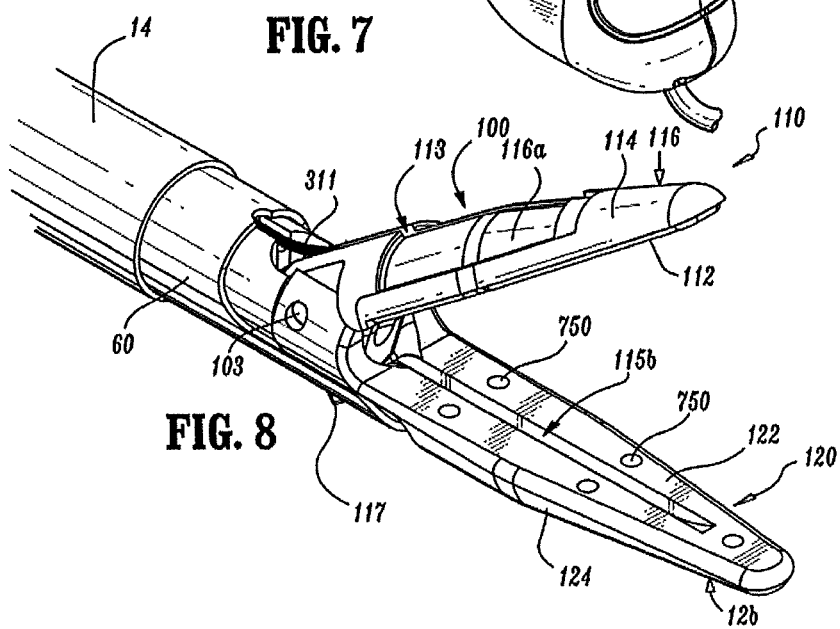
FIG. 8 is an enlarged, left perspective view of the end effector assembly with the jaw members shown in open configuration.
Figure 9:
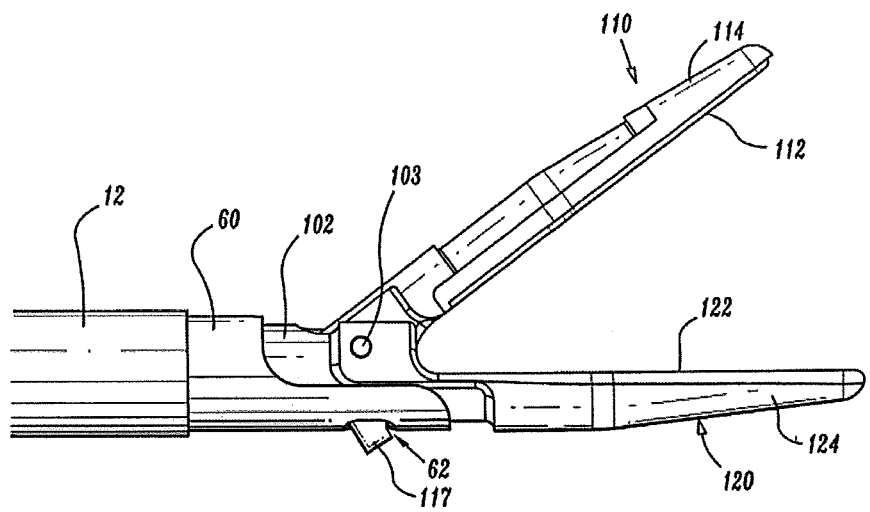
FIG. 9 is an enlarged, side view of the end effector assembly.
Figure 10:
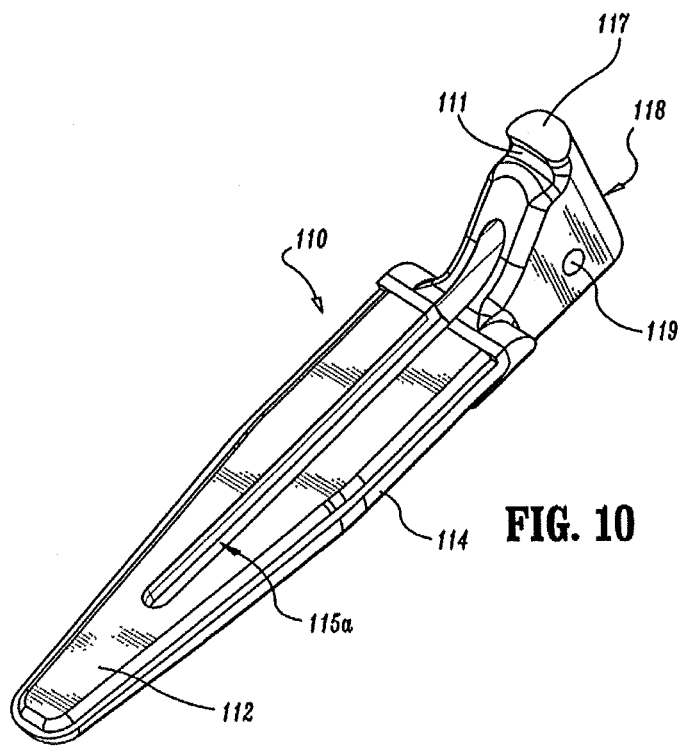
FIG. 10 is an enlarged, perspective view of the underside of the upper jaw member of the end effector assembly.
Figure 11:
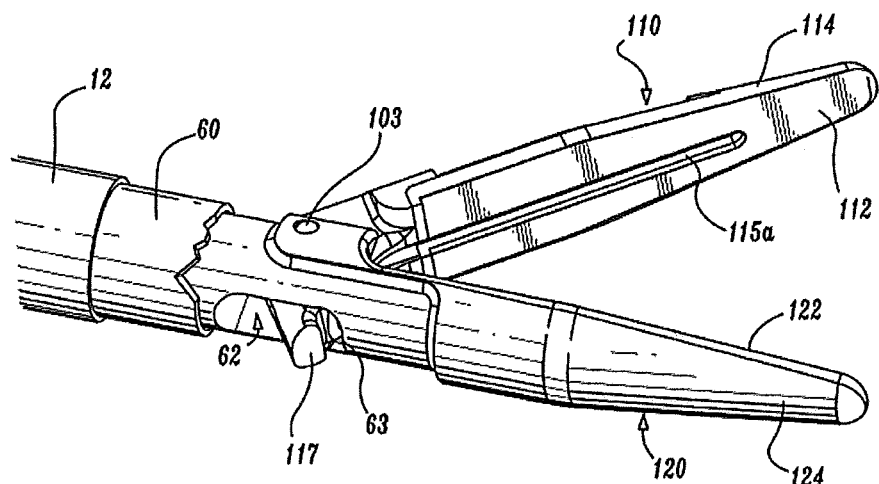
FIG. 11 is an enlarged, broken perspective view showing the end effector assembly and highlighting a cam-like closing mechanism which cooperates with a reciprocating pull sleeve to move the jaw members relative to one another.

As best illustrated in FIGS. 8 and 10, a knife channel 115a and 115b runs through the center of the jaw members 110 and 120, respectively, such that a blade 185 from the knife assembly 140 can cut the tissue 420 grasped between the jaw members 110 and 120 when the jaw members 110 and 120 are in a closed position. More particularly, the blade 185 can only be advanced through the tissue 420 when the jaw members 110 and 120 are closed thus preventing accidental or premature activation of the blade 185 through the tissue 420. Put simply, the knife channel 115 (made up of half channels 115a and 115b) is blocked when the jaws members 110 and 120 are opened and aligned for distal activation when the jaw members 110 and 120 are closed (See FIGS. 35 and 39). It is also envisioned that the unilateral end effector assembly 100 may be structured such that electrical energy can be routed through the sleeve 60 at the protrusion 117 contact point with the sleeve 60 or using a "brush" or lever (not shown) to contact the back of the movable jaw member 110 when the jaw member 110 closes. In this instance, the electrical energy would be routed through the protrusion 117 to the stationary jaw member 120. Alternatively, the cable lead 311 may be routed to energize the stationary jaw member 120 and the other electrical potential may be conducted through the sleeve 60 and transferred to the pivoting jaw member 110 which establishes electrical continuity upon retraction of the sleeve 60. It is envisioned that this particular envisioned embodiment will provide at least two important safety features: 1) the blade 185 cannot extend while the jaw members 110 and 120 are opened; and 2) electrical continuity to the jaw members 110 and 120 is made only when the jaw members are closed. The illustrated forceps 10 only includes the novel knife channel 115.

As best shown in FIG. 8, jaw member 110 also includes a jaw housing 116 which has an insulative substrate or insulator 114 and an electrically conducive surface 112. In one embodiment, insulator 114 is dimensioned to securely engage the electrically conductive sealing surface 112. This may be accomplished by stamping, by overmolding, by overmolding a stamped electrically conductive sealing plate and/or by overmolding a metal injection molded seal plate. For example and as shown in FIG. 17, the electrically conductive sealing plate 112 includes a series of upwardly extending flanges 111a and 111b which are designed to matingly engage the insulator 114. The insulator 114 includes a shoe-like interface 107 disposed at a distal end thereof which is dimensioned to engage the outer periphery 116a of the housing 116 in a slip-fit manner. The shoe-like interface 107 may also be overmolded about the outer periphery of the jaw 110 during a manufacturing step. It is envisioned that lead 311 terminates within the shoe-like interface 107 at the point where lead 311 electrically connects to the seal plate 112 (not shown). The movable jaw member 110 also includes a wire channel 113 which is designed to guide cable lead 311 into electrical continuity with sealing plate 112 as described in more detail below.

All of these manufacturing techniques produce jaw member 110 having an electrically conductive surface 112 which is substantially surrounded by an insulating substrate 114. The insulator 114, electrically conductive sealing surface 112 and the outer, non-conductive jaw housing 116 can be dimensioned to limit and/or reduce many of the known undesirable effects related to tissue sealing, e.g., flashover, thermal spread and stray current dissipation. Alternatively, it is also envisioned that the jaw members 110 and 120 may be manufactured from a ceramic-like material and the electrically conductive surface(s) 112 are coated onto the ceramic-like jaw members 110 and 120.

Jaw member 110 includes a pivot flange 118 which includes protrusion 117. Protrusion 117 extends from pivot flange 118 and includes an arcuately-shaped inner surface 111 dimensioned to matingly engage the aperture 62 of sleeve 60 upon retraction thereof. Pivot flange 118 also includes a pin slot 119 which is dimensioned to engage pivot pin 103 to allow jaw member 110 to rotate relative to jaw member 120 upon retraction of the reciprocating sleeve 60. As explained in more detail below, pivot pin 103 also mounts to the stationary jaw member 120 through a pair of apertures 101a and 101b disposed within a proximal portion of the jaw member 120.

It is envisioned that the electrically conductive sealing surface 112 may also include an outer peripheral edge which has a pre-defined radius and the insulator 114 meets the electrically conductive sealing surface 112 along an adjoining edge of the sealing surface 112 in a generally tangential position. In one embodiment, at the interface, the electrically conductive surface 112 is raised relative to the insulator 114. These and other envisioned embodiments are discussed in co-pending, commonly assigned Application Serial No. PCT/US01/11412 entitled "ELECTROSURGICAL INSTRUMENT WHICH REDUCES COLLATERAL DAMAGE TO ADJACENT TISSUE" by Johnson et al. and co-pending, commonly assigned Application Serial No. PCT/US01/11411 entitled "ELECTROSURGICAL INSTRUMENT WHICH IS DESIGNED TO REDUCE THE INCIDENCE OF FLASHOVER" by Johnson et al.

Figure 42:
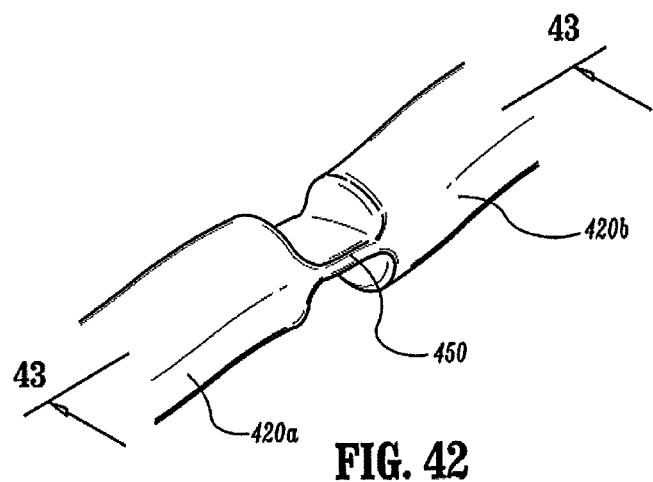
FIG. 42 is an enlarged view of a tissue seal.
Figure 43:
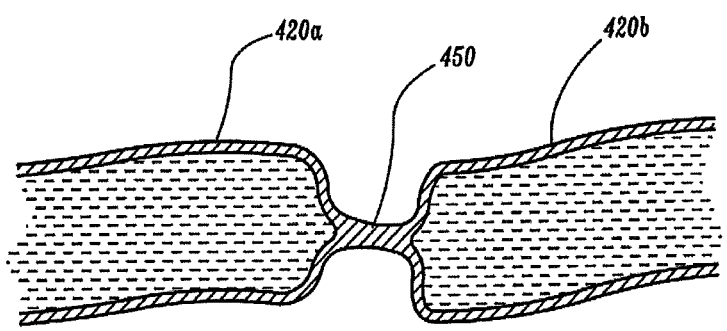
FIG. 43 is a side, cross section of a tissue seal.
Figure 46:
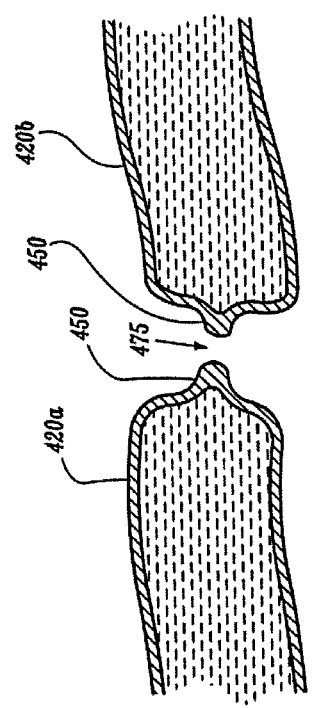
FIG. 46 is a side, cross section of a tissue seal after separation by the knife assembly.

In one embodiment, the electrically conductive surface 112 and the insulator 114, when assembled, form a longitudinally-oriented slot 115a defined therethrough for reciprocation of the knife blade 185. It is envisioned that the knife channel 115a cooperates with a corresponding knife channel 115b defined in stationary jaw member 120 to facilitate longitudinal extension of the knife blade 185 along a preferred cutting plane to effectively and accurately separate the tissue 420 along the formed tissue seal 450 (See FIGS. 42 and 46).

Jaw member 120 includes similar elements to jaw member 110 such as jaw housing 126 having an insulator 124 and an electrically conductive sealing surface 122 which is dimensioned to securely engage the insulator 124. Likewise, the electrically conductive surface 122 and the insulator 124, when assembled, include a longitudinally-oriented channel 115a defined therethrough for reciprocation of the knife blade 185. As mentioned above, when the jaw members 110 and 120 are closed about tissue 420, knife channels 115a and 115b form a complete knife channel 115 to allow longitudinal extension of the knife 185 in a distal fashion to sever tissue 420 along the tissue seal 450. It is also envisioned that the knife channel 115 may be completely disposed in one of the two jaw members, e.g., jaw member 120, depending upon a particular purpose. It is envisioned that the fixed jaw member 120 may be assembled in a similar manner as described above with respect to jaw member 110.

As best seen in FIG. 8, jaw member 120 includes a series of stop members 750 disposed on the inner facing surfaces of the electrically conductive sealing surface 122 to facilitate gripping and manipulation of tissue and to define a gap "G" (FIG. 41) between opposing jaw members 110 and 120 during sealing and cutting of tissue. It is envisioned that the series of stop members 750 may be employed on one or both jaw members 110 and 120 depending upon a particular purpose or to achieve a desired result. A detailed discussion of these and other envisioned stop members 750 as well as various manufacturing and assembling processes for attaching and/or affixing the stop members 750 to the electrically conductive sealing surfaces 112, 122 are described in commonly-assigned, co-pending U.S. Application Serial No. PCT/US01/11413 entitled "VESSEL SEALER AND DIVIDER WITH NON-CONDUCTIVE STOP MEMBERS" by Dycus et al.

Jaw member 120 is designed to be fixed to the end of a rotating tube 160 which is part of the rotating assembly 80 such that rotation of the tube 160 will impart rotation to the end effector assembly 100 (See FIGS. 25 and 27). Jaw member 120 includes a rear C-shaped cuff 170 having a slot 177 defined therein which is dimensioned to receive a slide pin 171. More particularly, slide pin 171 includes a slide rail 176 which extends substantially the length thereof which is dimensioned to slide into friction-fit engagement within slot 177. A pair of chamfered plates 172a and 172b extend generally radially from the slide rail 176 and include a radius which is substantially the same radius as the outer periphery of the rotating tube 160 such that the shaft 12 can encompass each of the same upon assembly.

As explained in more detail below, fixed jaw member 120 is connected to a second electrical potential through tube 160 which is connected at its proximal end to lead 310c. More particularly, fixed jaw 120 is welded to the rotating tube 160 and includes a fuse clip, spring clip or other electro-mechanical connection which provides electrical continuity to the fixed jaw member 120 from lead 310c (See FIG. 32). As best shown in FIGS. 25 and 26, the rotating tube 160 includes an elongated guide slot 167 disposed in an upper portion thereof which is dimensioned to carry lead 311 therealong. The chamfered plates 172a and 172b also form a wire channel 175 which is dimensioned to guide the cable lead 311 from the tube 160 and into the movable jaw member 110 (See FIG. 8). Lead 311 carries a first electrical potential to movable jaw 110. As explained in more detail below with respect to the internal electrical connections of the forceps, a second electrical connection from lead 310c is conducted through the tube 160 to the fixed jaw member 120.

As shown in FIG. 25, the distal end of the tube 160 is generally C-shaped to include two upwardly extending flanges 162a and 162b which define a cavity 165 for receiving the proximal end of the fixed jaw member 120 inclusive of C-shaped cuff 170 and slide pin 171 (See FIG. 27). In one embodiment, the tube cavity 165 retains and secures the jaw member 120 in a friction-fit manner; however, the jaw member 120 may be welded to the tube 160 depending upon a particular purpose. Tube 160 also includes an inner cavity 169 defined therethrough which reciprocates the knife assembly 140 upon distal activation thereof and an elongated guide rail 163 which guides the knife assembly 140 during distal activation. The details with respect to the knife assembly are explained in more detail with respect to FIGS. 21-24. The proximal end of tube 160 includes a laterally oriented slot 168 which is designed to interface with the rotating assembly 80 as described below.

FIG. 25 also shows the rotating assembly 80 which includes C-shaped rotating halves 82a and 82b which, when assembled about tube 160, form a generally circular rotating member 82. More particularly, each rotating half, e.g., 82b, includes a series of mechanical interfaces 375a, 375b, 375c and 375d which matingly engage a corresponding series of mechanical interfaces in half 82a to form rotating member 82. Half 82b also includes a tab 89b which together with a corresponding tab 89a disposed on half 82a (phantomly illustrated) cooperate to matingly engage slot 168 disposed on tube 160. As can be appreciated, this permits selective rotation of the tube 160 about axis "A" by manipulating the rotating member 82 in the direction of the arrow "B" (see FIG. 4).

As best shown in the exploded view of FIG. 17, jaw members 110 and 120 are pivotably mounted with respect to one another such that jaw member 110 pivots in a unilateral fashion from a first open position to a second closed position for grasping and manipulating tissue 420. More particularly, fixed jaw member 120 includes a pair of proximal, upwardly extending flanges 125a and 125b which define a cavity 121 dimensioned to receive flange 118 of movable jaw member 110 therein. Each of the flanges 125a and 125b includes an aperture 101a and 101b, respectively, defined therethrough which secures pivot pin 103 on opposite sides of pivot mount 119 disposed within jaw member 110. As explained in detail below with respect to the operation of the jaw members 110 and 120, proximal movement of the tube 60 engages detent 117 to pivot the jaw member 110 to a closed position.

FIGS. 13 and 14 show the details of the housing 20 and the component features thereof, namely, the drive assembly 150, the rotating assembly 80, the knife assembly 140, the trigger assembly 70 and the handles 40 and 50. More particularly, FIG. 13 shows the above-identified assemblies and components in an assembled form in the housing 20 and FIG. 14 shows an exploded view of each of the above-identified assemblies and components.

As shown best in FIG. 14, the housing includes halves 20a and 20b which, when mated, form housing 20. As can be appreciated, housing 20, once formed, houses the various assemblies identified above which will enable a user to selectively manipulate, grasp, seal and sever tissue 420 in a simple, effective, and efficient manner. In one embodiment, each half of the housing, e.g., half 20b, includes a series of mechanical interfacing component, e.g., 27a-27f which align and/or mate with a corresponding series of mechanical interfaces (not shown) to align the two housing halves 20a and 20b about the inner components and assemblies. In one embodiment, the housing halves 20a and 20b are then sonic welded to secure the housing halves 20a and 20b once assembled.

As mentioned above, the movable handle 40 includes clevis 45 which forms upper flanges 45a and 45b which pivot about pins 29a and 29b to pull the reciprocating sleeve 60 along longitudinal axis "A" and force during flange 47 against the drive assembly 150 which, in turn, closes the jaw members 110 and 120. As mentioned above, the lower end of the movable handle 40 includes a flange 90 which has a t-shaped distal end 95 which rides within a predefined channel 51 disposed within fixed handle 50 to lock the movable handle 40 in a preset orientation relative to the fixed handle 50. The arrangement of the upper flanges 45a and 45b and the pivot point of the movable handle 40 provides a distinct mechanical advantage over conventional handle assemblies due to the unique position of the pivot pins 29a and 29b (i.e., pivot point) relative to the longitudinal axis "A" of the driving flange 47. In other words, by positioning the pivot pins 29a and 29b above the driving flange 47, the user gains lever-like mechanical advantage to actuate the jaw members 110 and 120. This reduces the overall amount of mechanical force necessary to close the jaw members 110 and 120 to effect a tissue seal.

Handle 40 also includes a finger loop 41 which defines opening 42 which is dimensioned to facilitate grasping the handle 40. In one embodiment, finger loop 41 includes rubber insert 43 which enhances the overall ergonomic "feel" of the handle member 40. A locking flange 44 is disposed on the outer periphery of the handle member 40 above the finger loop 41. Locking flange 44 prevents the trigger assembly 70 from firing when the handle member 40 is oriented in a non-actuated position, i.e., the jaw members 110 and 120 are open. As can be appreciated, this prevents accidental or premature severing of tissue 420 prior to completion of the tissue seal 450.

Fixed handle 50 includes halves 50a and 50b which, when assembled, form handle 50. Fixed handle 50 includes a channel 51 defined therein which is dimensioned to receive flange 90 in a proximal moving manner when movable handle 40 is actuated. The t-shaped free end 95 of handle 40 is dimensioned for facile reception within channel 51 of handle 50. It is envisioned that flange 90 may be dimensioned to allow a user to selectively, progressively and/or incrementally move jaw members 110 and 120 relative to one another from the open to closed positions. For example, it is also contemplated that flange 90 may include a ratchet-like interface which lockingly engages the movable handle 40 and, therefore, jaw members 110 and 120 at selective, incremental positions relative to one another depending upon a particular purpose. Other mechanisms may also be employed to control and/or limit the movement of handle 40 relative to handle 50 (and jaw members 110 and 120) such as, e.g., hydraulic, semi-hydraulic, linear actuator(s), gas-assisted mechanisms and/or gearing systems.

As best illustrated in FIG. 13, housing halves 20a and 20b when assembled form an internal cavity 52 which predefines the channel 51 within fixed handle 50 such that an entrance pathway 54 and an exit pathway 58 are formed for reciprocation of the t-shaped flange end 95 therein. When assembled, two generally triangular-shaped members 57 (one disposed in each handle half 50a and 50b) are positioned in close abutment relative to one another to define a rail or track 192 therebetween. During movement of the flange 90 along the entrance and exit pathways 54 and 58, respectively, the t-shaped end 95 rides along track 192 between the two triangular members 57 according to the particular dimensions of the triangularly-shaped members 57, which, as can be appreciated, predetermines part of the overall pivoting motion of handle 40 relative to fixed handle 50.

Once actuated, handle 40 moves in a generally arcuate fashion towards fixed handle 50 about pivot pins 29a and 29b which forces driving flange 47 proximally against the drive assembly 150 which, in turn, pulls reciprocating sleeve 60 in a generally proximal direction to close jaw member 110 relative to jaw member 120. Moreover, proximal rotation of the handle 40 causes the locking flange 44 to release, i.e., "unlock", the trigger assembly 70 for selective actuation. This feature is shown in detail with reference to FIGS. 33, 37 and 44 and the explanation of the operation of the knife assembly 70 explained below.

The operating features and relative movements of the internal working components of the forceps 10 are shown by phantom representation in the various figures. As mentioned above, when the forceps 10 is assembled a predefined channel 52 is formed within the fixed handle 50. The channel includes entrance pathway 51 and an exit pathway 58 for reciprocation of the flange 90 and the t-shaped end 95 therein. Once assembled, the two generally triangular-shaped members 57 are positioned in close abutment relative to one another and define track 192 disposed therebetween.

As the handle 40 is squeezed and flange 90 is incorporated into channel 51 of fixed handle 50, the driving flange 47, through the mechanical advantage of the above-the-center pivot points, biases flange 154 of drive ring 159 which, in turn, compresses a spring 67 against a rear ring 156 of the drive assembly 150 (FIG. 40). As a result thereof, the rear ring 156 reciprocates sleeve 60 proximally which, in turn, closes jaw member 110 onto jaw member 120. It is envisioned that the utilization of an over-the-center pivoting mechanism will enable the user to selectively compress the coil spring 67 a specific distance which, in turn, imparts a specific pulling load on the reciprocating sleeve 60 which is converted to a rotational torque about the jaw pivot pin 103. As a result, a specific closure force can be transmitted to the opposing jaw members 110 and 120.

FIGS. 37 and 38 show the initial actuation of handle 40 towards fixed handle 50 which causes the free end 95 of flange 90 to move generally proximally and upwardly along entrance pathway 51. During movement of the flange 90 along the entrance and exit pathways 51 and 58, respectively, the t-shaped end 95 rides along track 192 between the two triangular members 57. Once the desired position for the sealing site is determined and the jaw members 110 and 120 are properly positioned, handle 40 may be compressed fully such that the t-shaped end 95 of flange 90 clears a predefined rail edge 193 located atop the triangular-shaped members 57. Once end 95 clears edge 193, releasing movement of the handle 40 and flange 90 is redirected into a catch basin 194 located at the proximal end of the triangular member 57. More particularly, upon a slight reduction in the closing pressure of handle 40 against handle 50, the handle 40 returns slightly distally towards entrance pathway 51 but is re-directed towards exit pathway 58. At this point, the release or return pressure between the handles 40 and 50 which is attributable and directly proportional to the release pressure associated with the compression of the drive assembly 150 causes the end 95 of flange 90 to settle or lock within catch basin 194. Handle 40 is now secured in position within fixed handle 50 which, in turn, locks the jaw members 110 and 120 in a closed position against the tissue 420.

Figure 4:
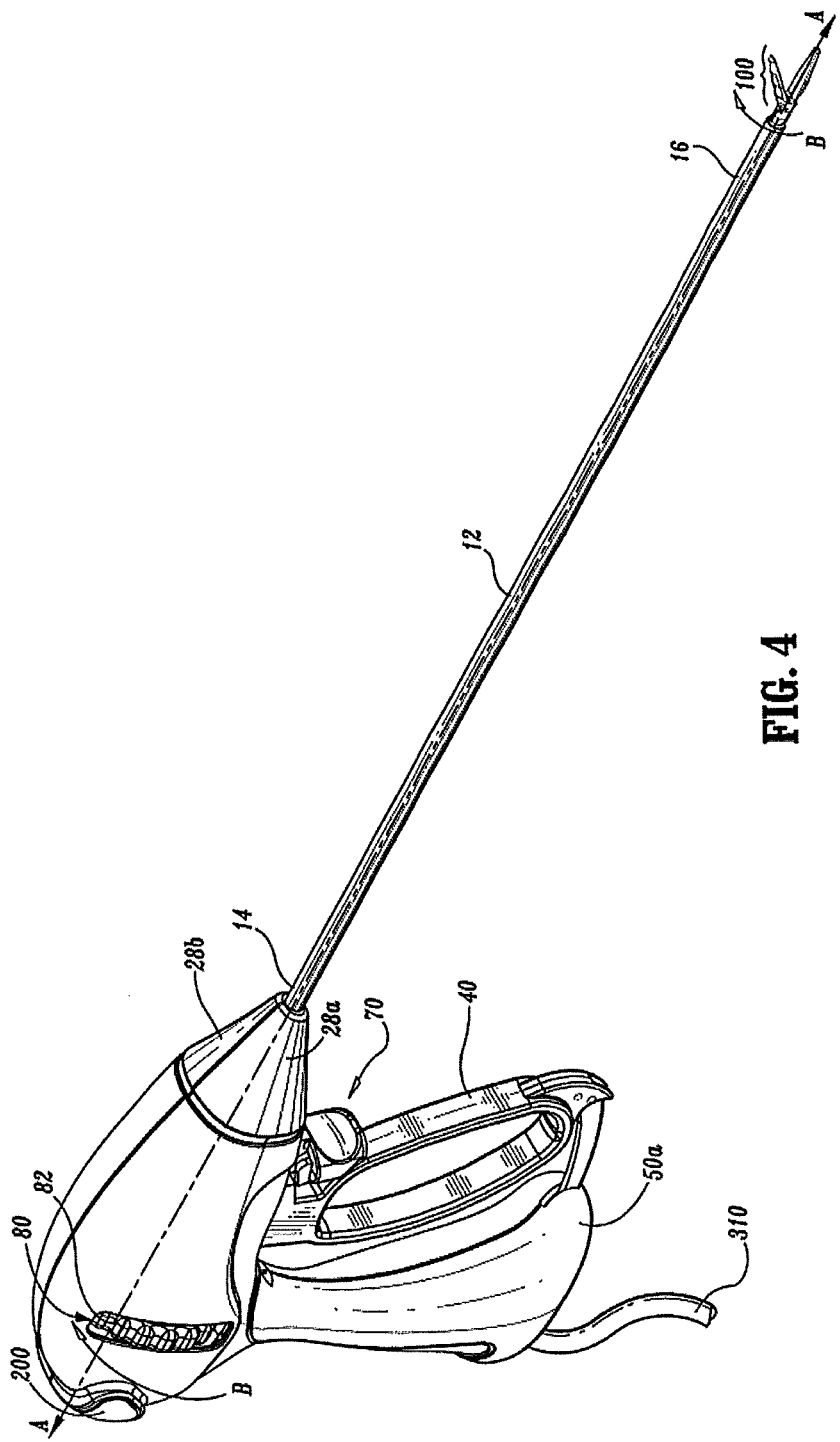
FIG. 4 is a perspective view of the forceps of FIG. 1 showing the rotation of the end effector assembly about a longitudinal axis "A"
Figure 7:
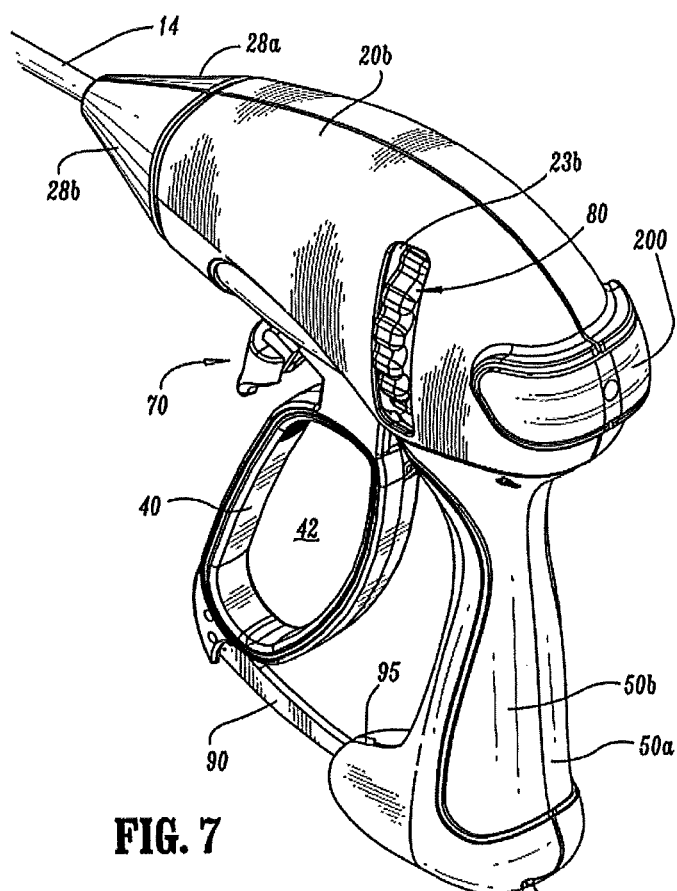
FIG. 7 is an enlarged, rear perspective view of the housing.

As mentioned above, the jaw members 110 and 120 may be opened, closed and rotated to manipulate tissue 420 until sealing is desired. This enables the user to position and reposition the forceps 10 prior to activation and sealing. As illustrated in FIG. 4, the end effector assembly 100 is rotatable about longitudinal axis "A" through rotation of the rotating assembly 80. As explained in more detail below, it is envisioned that the unique feed path of the cable lead 311 through the rotating assembly 80, along shaft 12 and, ultimately, to the jaw member 110 enables the user to rotate the end effector assembly 100 about 180 degrees in both the clockwise and counterclockwise direction without tangling or causing undue strain on cable lead 311. Cable lead 310c is fused or clipped to the proximal end of tube 160 and is generally unaffected by rotation of the jaw members 110 and 120. As can be appreciated, this facilitates the grasping and manipulation of tissue 420.

Again as best shown in FIGS. 13 and 14, trigger assembly 70 mounts atop movable handle 40 and cooperates with the knife assembly 140 to selectively translate knife 185 through a tissue seal 450. More particularly, the trigger assembly 70 includes a finger actuator 71 and a U-shaped upwardly-extending flange 74 having legs 74a and 74b. A pivot pin 73 mounts the trigger assembly 70 between housing halves 20a and 20b for selective rotation thereof. A pair of safety tabs 76a and 76b are disposed atop finger actuator 71 and are dimensioned to abut the locking flange 44 on handle 40 when the handle 40 is disposed in a non-actuated position, i.e., the jaw members 110 and 120 are opened.

As best seen in FIG. 14, the legs 74a and 74b of the U-shaped flange 74 each include a respective slot 77a and 77b defined therein which are each dimensioned to receive a free end of an elongated drive bar 75. Drive bar 75, in turn, is dimensioned to sit within a drive slot 147 which is part of the knife assembly 140 explained in detail below. The trigger assembly 70 is mounted atop the donut-like drive ring 141 of the knife assembly 140. Proximal activation of the finger actuator 71 rotates the trigger assembly 70 about pivot pin 73 which, in turn, forces the drive bar 75 distally, which, as explained in more detail below, ultimately extends the knife 185 through the tissue 420. A spring 350 biases the knife assembly 70 in a retracted position such that after severing tissue 420 the knife 185 and the knife assembly 70 are automatically returned to a pre-firing position.

As mentioned above, the locking flange 44 abuts tabs 76a and 76b when the handle 40 is disposed in a non-actuated position. When the handle 40 is actuated and flange 90 is fully reciprocated within channel 51 of the fixed handle 50, the locking flange 44 moves proximally allowing activation of the trigger assembly 70 (See FIGS. 37 and 44).

Drive assembly 150 includes reciprocating sleeve 60, drive housing 158, spring 67, drive ring 159, drive stop 155 and guide sleeve 157 which all cooperate to form the drive assembly 150. More particularly and as best shown in FIGS. 28 and 29, the reciprocating sleeve 60 includes a distal end 65 which as mentioned above has an aperture 62 formed therein for actuating the detent 117 of jaw member 110. In one embodiment, the distal end 65 includes a scoop-like support member 69 for supporting the proximal end of the fixed jaw member 120 therein. The proximal end 61 of the reciprocating sleeve 60 includes a slot 68 defined therein which is dimensioned to slidingly support the knife assembly 70 for longitudinal reciprocation thereof to sever tissue 420. The slot 68 also permits retraction of the reciprocating sleeve 60 over the knife assembly 140 during the closing of jaw member 110 relative to jaw member 120.

Figures 18, 19, 20:
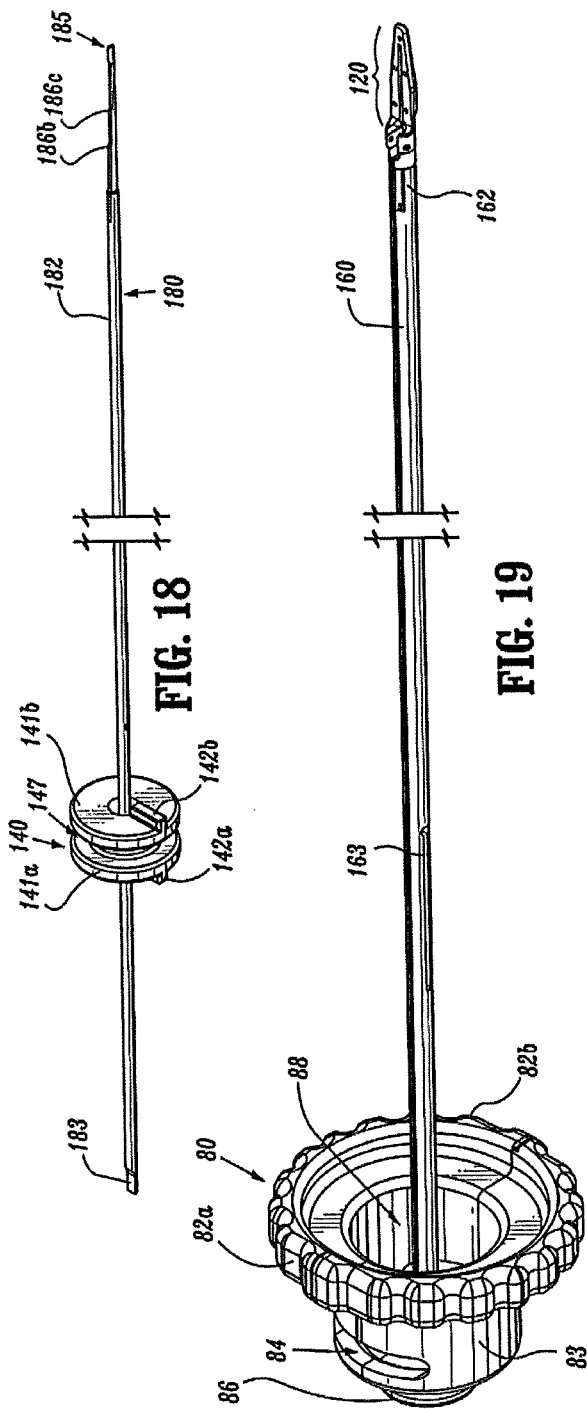
FIG. 18 is an enlarged, perspective view of the knife assembly.
FIG. 19 is an enlarged, perspective view of the rotating assembly.
FIG. 20 is an enlarged, perspective view of the drive assembly.
Figure 21:
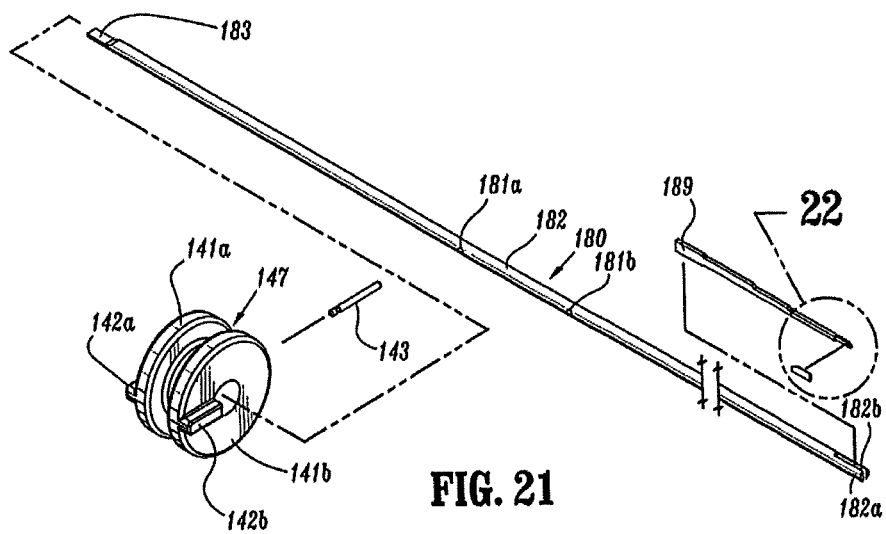
FIG. 21 is an enlarged, perspective view of the knife assembly with parts separated.
Figure 22:
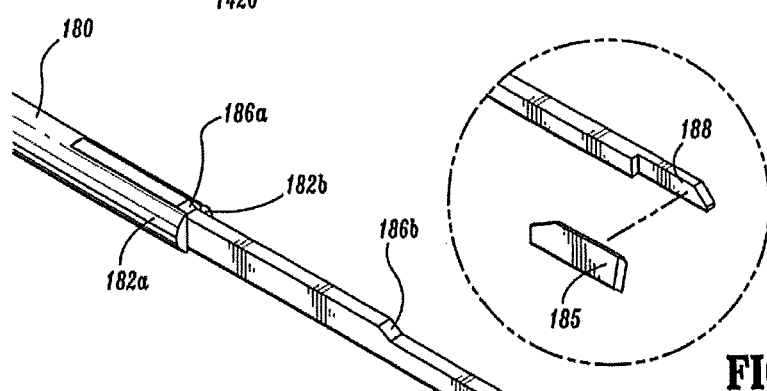
FIG. 22 is a greatly-enlarged view of the indicated area of detail of FIG. 21.
Figure 23:
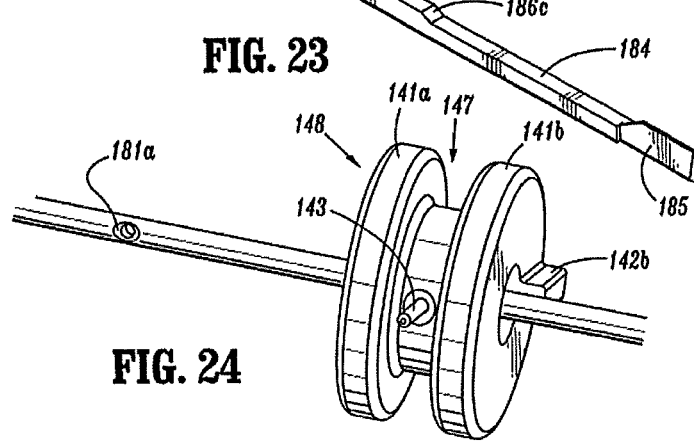
FIG. 23 is a greatly-enlarged, perspective view of a distal end of the knife assembly.
Figure 24:
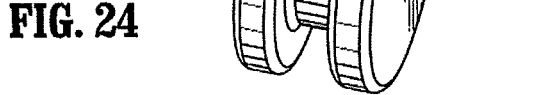
FIG. 24 is a greatly-enlarged, perspective view of a knife drive of the knife assembly.

The proximal end 61 of the reciprocating sleeve 60 is positioned within an aperture 151 in drive housing 158 to permit selective reciprocation thereof upon actuation of the movable handle 40. The spring 67 is assembled atop the drive housing 158 between a rear stop 156 of the drive housing 158 and a forward stop 154 of the drive ring 159 such that movement of the forward stop 154 compresses the spring 67 against the rear stop 156 which, in turn, reciprocates the drive sleeve 60. As a result thereof, the jaw members 110 and 120 and the movable handle 40 are biased by spring 67 in an open configuration. The drive stop 155 is fixedly positioned atop the drive housing 158 and biases the upper flanges 45a and 45b of the movable handle 40 when actuated such that the driving flange 47 forces the stop 154 of the drive ring 159 proximally against the force of the spring 67. The spring 67, in turn, forces the rear stop 156 proximally to reciprocate the sleeve 60 (See FIG. 40). In one embodiment, the rotating assembly 80 is located proximal to the driving flange 47 to facilitate rotation of the end effector assembly 100. The guide sleeve 157 mates with the proximal end 61 of the reciprocating sleeve 60 and affixes to the drive housing 158. The assembled drive assembly 150 is shown best in FIG. 20.

As best shown in FIGS. 18 and 21-24, the knife assembly 140 includes an elongated rod 182 having a bifurcated distal end comprising prongs 182a and 182b which cooperate to receive a knife bar 184 therein. The knife assembly 180 also includes a proximal end 183 which is keyed to facilitate insertion into tube 160 of the rotating assembly 80. A knife wheel 148 is secured to the knife bar 182 by a pin 143. More particularly, the elongated knife rod 182 includes apertures 181a and 181b which are dimensioned to receive and secure the knife wheel 148 to the knife rod 182 such that longitudinal reciprocation of the knife wheel 148, in turn, moves the elongated knife rod 182 to sever tissue 420.

In one embodiment, the knife wheel 148 is donut-like and includes rings 141a and 141b which define a drive slot 147 designed to receive the drive bar 75 of the trigger assembly 70 such that proximal actuation of the trigger assembly 70 forces the drive bar 75 and the knife wheel 148 distally. It is envisioned that aperture 181a may be used for a particular trigger assembly 70 configuration and aperture 181b may be used for a different trigger assembly 70 configuration. As such, pin 143 is designed for attachment through either aperture 181a or 181b to mount the knife wheel 148 (See FIG. 24). Knife wheel 148 also includes a series of radial flanges 142a and 142b which are dimensioned to slide along both channel 163 of tube 160 and slot 68 of the reciprocating sleeve 60 (See FIG. 15).

As mentioned above, the knife rod 182 is dimensioned to mount the knife bar 184 between prongs 182a and 182b, which can be in a friction-fit engagement. The knife bar 184 includes a series of steps 186a, 186b and 186c which reduce the profile of the knife bar 184 towards the distal end thereof. The distal end of the knife bar 184 includes a knife support 188 which is dimensioned to retain knife blade 185. The end of the knife support can include a chamfered edge 188a. It is envisioned that the knife blade 185 may be welded to the knife support 188 of secured in any manner known in the trade.

As best shown in the exploded view of the FIGS. 14 and 30-32, the electrical leads 310a, 310b, 310c and 311 are fed through the housing 20 by electrosurgical cable 310. More particularly, the electrosurgical cable 310 is fed into the bottom of the housing 20 through fixed handle 50. Lead 310c extends directly from cable 310 into the rotating assembly 80 and connects (via a fused clip or spring clip or the like) to tube 60 to conduct the second electrical potential to fixed jaw member 120. Leads 310a and 310b extend from cable 310 and connect to the hand switch or joy-stick-like toggle switch 200.

Switch 200 includes an ergonomically dimensioned toggle plate 205 having a pair of wings 207a and 207b which may conform to the outer shape of housing 20 (once assembled). It is envisioned that the switch 200 permits the user to selectively activate the forceps 10 in a variety of different orientations, i.e., multi-oriented activation. As can be appreciated, this simplifies activation. A pair of prongs 204a and 204b extend distally and mate with a corresponding pair of mechanical interfaces 21a and 21b disposed within housing 20 (See FIG. 32). In one embodiment, prongs 204a and 204b snap-fit to the housing 20 during assembly. Toggle plate 205 also includes a switch interface 203 with mates with a switch button 202 which, in turn, connects to electrical interface 201. The electrical leads 310a and 310b are electrically connected to electrical interface 201. When the toggle plate 205 is depressed, trigger lead 311 carries the first electrical potential to jaw member 110. More particularly, lead 311 extends from interface 201 through a plurality of slots 84a, 84b and 84c of the rotating assembly 80 (See FIGS. 25 and 30) and along the upper portion of tube 160 and eventually connects to the movable jaw member 110 as described above (See FIGS. 32, 34 and 35).

When the switch 200 is depressed, electrosurgical energy is transferred through leads 311 and 310c to jaw members 110 and 120, respectively. It is envisioned that a safety switch or circuit (not shown) may be employed such that the switch cannot fire unless the jaw members 110 and 120 are closed and/or unless the jaw members 110 and 120 have tissue 420 held therebetween. In the latter instance, a sensor (not shown) may be employed to determine if tissue 420 is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR" filed on May 1, 2003, now issued U.S. Pat. No. 7,137,980.

In one embodiment, the jaw members 110 and 120 are electrically isolated from one another such that electrosurgical energy can be effectively transferred through the tissue 420 to form seal 450. For example and as best illustrated in FIGS. 32, 34 and 35, each jaw member, e.g., 110, includes a uniquely-designed electrosurgical cable path disposed therethrough which transmits electrosurgical energy to the electrically conductive sealing surface 112. It is envisioned that jaw member 110 may include one or more cable guides or crimp-like electrical connectors to direct cable lead 311 towards electrically conductive sealing surface 112. In one embodiment, cable lead 311 is held loosely but securely along the cable path to permit rotation of the jaw member 110 about pivot 103. As can be appreciated, this isolates electrically conductive sealing surface 112 from the remaining operative components of the end effector assembly 100, jaw member 120 and shaft 12. As explained in detail above, the second electrical potential is conducted to jaw member 120 through tube 160. The two potentials are isolated from one another by virtue of the insulative sheathing surrounding cable lead 311.

It is contemplated that utilizing a cable feed path for cable lead 311 and by utilizing a conductive tube 160 to carry the first and second electrical potentials not only electrically isolates each jaw member 110 and 120 but also allows the jaw members 110 and 120 to pivot about pivot pin 103 without unduly straining or possibly tangling cable lead 311. Moreover, it is envisioned that the simplicity of the electrical connections greatly facilitates the manufacturing and assembly process and assures a consistent and tight electrical connection for the transfer of energy through the tissue 420.

As mentioned above, it is envisioned that cable leads 311 and 310c are fed through respective halves 82a and 82b of the rotating assembly 80 in such a manner to allow rotation of the shaft 12 (via rotation of the rotating assembly 80) in the clockwise or counter-clockwise direction without unduly tangling or twisting the cable leads 311 and 310c. More particularly, each cable lead 311 and 310c is fed through a series of conjoining slots 84a, 84b, 84c and 84d located in the two halves 82a and 82b of the rotating assembly 80. In one embodiment, each conjoining pair of slots, e.g., 84a, 84b and 84c, 84d, are large enough to permit rotation of the rotating assembly 80 without unduly straining or tangling the cable leads 311 and 310c. The presently disclosed cable lead feed path is envisioned to allow rotation of the rotation assembly approximately 180 degrees in either direction.

Turning back to FIG. 14 which shows the exploded view of the housing 20, rotating assembly 80, trigger assembly 70, movable handle 40 and fixed handle 50, it is envisioned that all of these various component parts along with the shaft 12 and the end effector assembly 100 are assembled during the manufacturing process to form a partially and/or fully disposable forceps 10. For example and as mentioned above, the shaft 12 and/or end effector assembly 100 may be disposable and, therefore, selectively/releasably engagable with the housing 20 and rotating assembly 80 to form a partially disposable forceps 10 and/or the entire forceps 10 may be disposable after use.

As best seen in FIG. 13, once assembled, spring 67 is poised for compression atop drive housing 158 upon actuation of the movable handle 40. More particularly, movement of the handle 40 about pivot pins 29a and 29b reciprocates the flange 90 into fixed handle 50 and forces drive flange 47 against flange 154 of drive ring 159 to compress spring 67 against the rear stop 156 to reciprocate the sleeve 60 (See FIG. 40).

In one embodiment, the trigger assembly 70 is initially prevented from firing by the locking flange 44 disposed on movable handle 40 which abuts against the trigger assembly 70 prior to actuation. It is envisioned that the opposing jaw members 110 and 120 may be rotated and partially opened and closed without unlocking the trigger assembly 70 which, as can be appreciated, allows the user to grip and manipulate the tissue 420 without premature activation of the knife assembly 140. As mentioned below, only when the t-shaped end 95 of flange 90 is completely reciprocated within channel 51 of the fixed handle 50 and seated within pre-defined catch basin 194 will the locking flange allow activation of the trigger assembly 70. The operating features and relative movements of these internal working components of the forceps 10 are shown by phantom representation and directional arrows and are best illustrated in FIGS. 36-49.

FIG. 36 shows the forceps approximating tissue. As the handle 40 is squeezed and flange 90 is incorporated into channel 54 of fixed handle 50, the drive flange 47, through the mechanical advantage of the over the center pivot pins 29a and 29b is rotated generally proximally to compress spring 67. Simultaneously, the reciprocating sleeve 60 is pulled proximally by the movement of rear ring 156 which, in turn, causes aperture 62 of sleeve 60 to proximally cam detent 117 and close the jaw member 110 relative to jaw member 120 (See FIGS. 37-40).

It is envisioned that the mechanical advantage of the over-the-center pivot will enable the user to selectively compress the coil spring 67 a specific distance which, in turn, imparts a specific load on the reciprocating sleeve 60. The reciprocating sleeve's 60 load is converted to a torque about the jaw pivot 103. As a result, a specific closure force can be transmitted to the opposing jaw members 110 and 120. As mentioned above, the jaw members 110 and 120 may be opened, closed and rotated to manipulate tissue 420 until sealing is desired without unlocking the trigger assembly 70. This enables the user to position and re-position the forceps 10 prior to activation and sealing. More particularly, as illustrated in FIG. 4, the end effector assembly 100 is rotatable about longitudinal axis "A" through rotation of the rotating assembly 80.

Once the desired position for the sealing site is determined and the jaw members 110 and 120 are properly positioned, handle 40 may be compressed fully such that the t-shaped end 95 of flange 90 clears a predefined rail edge 193 located atop the triangular-shaped members 57. Once end 95 clears edge 193, the end is directed into catch basin 194 located within the exit pathway 58. More particularly, upon a slight reduction in the closing pressure of handle 40 against handle 50, the handle 40 returns slightly distally towards entrance pathway 54 but is re-directed towards exit pathway 58 into catch basin 194 (See FIG. 38). At this point, the release or return pressure between the handles 40 and 50 which is attributable and directly proportional to the release pressure associated with the compression of the drive assembly 150 causes the end 95 of flange 90 to settle or lock within catch basin 194. Handle 40 is now secured in position within fixed handle 50 which, in turn, locks the jaw members 110 and 120 in a closed position against the tissue 420.

Figure 44:
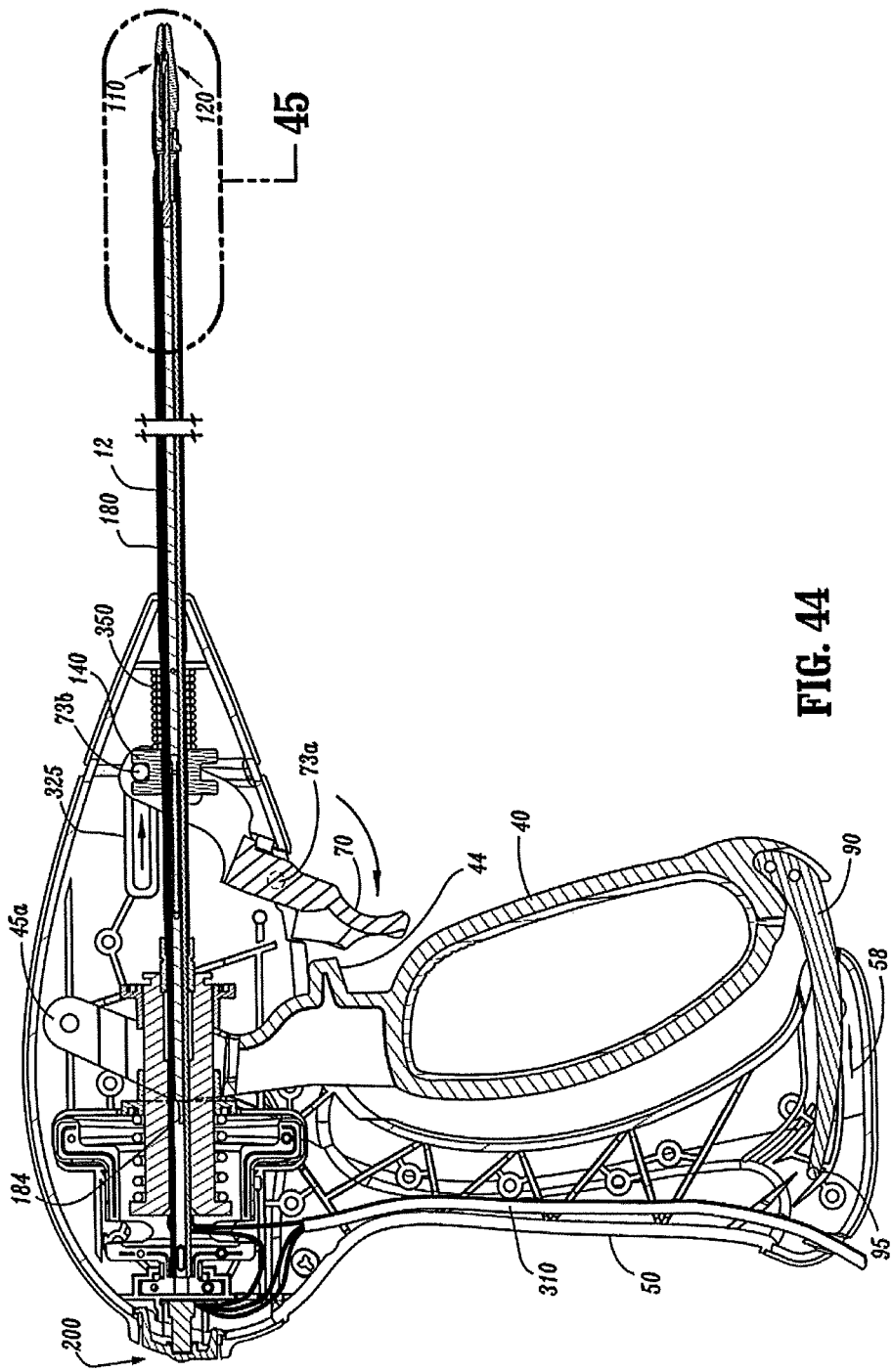
FIG. 44 is a cross section of the housing with the handle in a locked configuration and showing the moving components of the knife assembly during activation.
Figure 45:
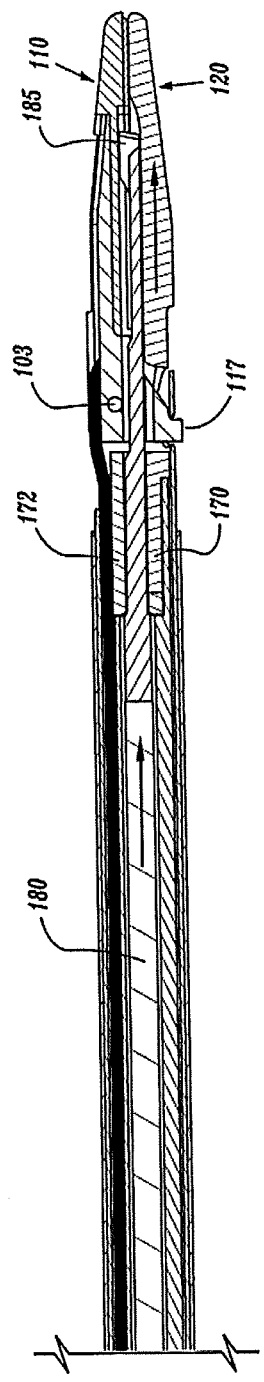
FIG. 45 is an enlarged view of the area indicated in detail in FIG. 44.

At this point the jaws members 110 and 120 are fully compressed about the tissue 420 (FIG. 41). Moreover, the forceps 10 is now ready for selective application of electrosurgical energy and subsequent separation of the tissue 420, i.e., as t-shaped end 95 seats within catch basin 194, locking flange 44 moves into a position to permit activation of the trigger assembly 70 (FIGS. 44 and 45).

As the t-shaped end 95 of flange 90 becomes seated within catch basin 194, a proportional axial force on the reciprocating sleeve 60 is maintained which, in turn, maintains a compressive force between opposing jaw members 110 and 120 against the tissue 420. It is envisioned that the end effector assembly 100 and/or the jaw members 110 and 120 may be dimensioned to off-load some of the excessive clamping forces to prevent mechanical failure of certain internal operating elements of the end effector 100.

As can be appreciated, the combination of the mechanical advantage of the over-the-center pivot along with the compressive force associated with the compression spring 67 facilitate and assure consistent, uniform and accurate closure pressure about the tissue 420 within the desired working pressure range of about 3 kg/cm² to about 16 kg/cm² and, preferably, about 7 kg/cm² to about 13 kg/cm². By controlling the intensity, frequency and duration of the electrosurgical energy applied to the tissue 420, the user can either cauterize, coagulate/desiccate, seal and/or simply reduce or slow bleeding. As mentioned above, two mechanical factors play an important role in determining the resulting thickness of the sealed tissue and effectiveness of the seal 450, i.e., the pressure applied between opposing jaw members 110 and 120 and the gap distance "G" between the opposing sealing surfaces 112, 122 of the jaw members 110 and 120 during the sealing process. However, thickness of the resulting tissue seal 450 cannot be adequately controlled by force alone. In other words, too much force and the two jaw members 110 and 120 would touch and possibly short resulting in little energy traveling through the tissue 420 thus resulting in a bad tissue seal 450. Too little force and the seal 450 would be too thick.

Applying the correct force is also important for other reasons: to oppose the walls of the vessel; to reduce the tissue impedance to a low enough value that allows enough current through the tissue 420; and to overcome the forces of expansion during tissue heating in addition to contributing towards creating the required end tissue thickness which is an indication of a good seal 450.

In one embodiment, the electrically conductive sealing surfaces 112, 122 of the jaw members 110, 120, respectively, are relatively flat to avoid current concentrations at sharp edges and to avoid arcing between high points. In addition and due to the reaction force of the tissue 420 when engaged, jaw members 110 and 120 can be manufactured to resist bending. For example, the jaw members 110 and 120 may be tapered along the width thereof which is advantageous for two reasons: 1) the taper will apply constant pressure for a constant tissue thickness at parallel; 2) the thicker proximal portion of the jaw members 110 and 120 will resist bending due to the reaction force of the tissue 420.

As mentioned above, at least one jaw member, e.g., 120, may include a stop member 750 which limits the movement of the two opposing jaw members 110 and 120 relative to one another. In one embodiment, the stop member 750 extends from the sealing surface 122 a predetermined distance according to the specific material properties (e.g., compressive strength, thermal expansion, etc.) to yield a consistent and accurate gap distance "G" during sealing (FIG. 41). It is envisioned for the gap distance between opposing sealing surfaces 112 and 122 during sealing ranges from about 0.001 inches to about 0.006 inches and, more preferably, between about 0.002 and about 0.003 inches. In one embodiment, the non-conductive stop members 750 are molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 750. Several thermal spraying techniques are contemplated which involve depositing a broad range of heat resistant and insulative materials on various surfaces to create stop members 750 for controlling the gap distance between electrically conductive surfaces 112 and 122.

As energy is being selectively transferred to the end effector assembly 100, across the jaw members 110 and 120 and through the tissue 420, a tissue seal 450 forms isolating two tissue halves 420a and 420b. At this point and with other known vessel sealing instruments, the user may remove and replace the forceps 10 with a cutting instrument (not shown) to divide the tissue halves 420a and 420b along the tissue seal 450. As can be appreciated, this is both time consuming and tedious and may result in inaccurate tissue division across the tissue seal 450 due to misalignment or misplacement of the cutting instrument along the ideal tissue cutting plane.

As explained in detail above, the present disclosure incorporates knife assembly 140 which, when activated via the trigger assembly 70, progressively and selectively divides the tissue 420 along an ideal tissue plane in precise manner to effectively and reliably divide the tissue 420 into two sealed halves 420a and 420b (See FIG. 46) with a tissue gap 475 therebetween. The knife assembly 140 allows the user to quickly separate the tissue 420 immediately after sealing without substituting a cutting instrument through a cannula or trocar port. As can be appreciated, accurate sealing and dividing of tissue 420 is accomplished with the same forceps 10.

It is envisioned that knife blade 185 may also be coupled to the same or an alternative electrosurgical energy source to facilitate separation of the tissue 420 along the tissue seal 450 (not shown). Moreover, it is envisioned that the angle of the knife blade tip 185 may be dimensioned to provide more or less aggressive cutting angles depending upon a particular purpose. For example, the knife blade 185 may be positioned at an angle which reduces "tissue wisps" associated with cutting. More over, the knife blade 185 may be designed having different blade geometries such as serrated, notched, perforated, hollow, concave, convex etc. depending upon a particular purpose or to achieve a particular result.

Once the tissue 420 is divided into tissue halves 420*a* and 420*b*, the jaw members 110 and 120 may be opened by re-grasping the handle 40 as explained below. It is envisioned that the knife assembly 140 generally cuts in a progressive, uni-directional fashion (i.e., distally).

As best shown in FIGS. 47-49, re-initiation or re-grasping of the handle 40 again moves t-shaped end 95 of flange 90 generally proximally along exit pathway 58 until end 95 clears a lip 196 disposed atop triangular-shaped members 57 along exit pathway 58. Once lip 196 is sufficiently cleared, handle 40 and flange 90 are fully and freely releasable from handle 50 along exit pathway 58 upon the reduction of grasping/gripping pressure which, in turn, returns the jaw members 110 and 120 to the open, pre-activated position.

As discussed above, it is envisioned that multiple end effector assemblies may be substituted for the end effector assembly 100 previously described. It will be understood that the description of the forceps 10 coupled with the end effector assembly 100 is applicable to the forceps 10 coupled with the end effector assembly 500, described below.

An alternate embodiment of an end effector is shown in FIGS. 52-55. The end effector assembly 500 may be engaged at the distal end 16 of shaft 12 and includes a pair of opposing jaw members, 510 and 520.

The end effector assembly 500 is designed as a unilateral assembly, e.g., jaw member 520 is fixed relative to the shaft 12 and jaw member 510 pivots about a pivot pin 503.

Figure 53:
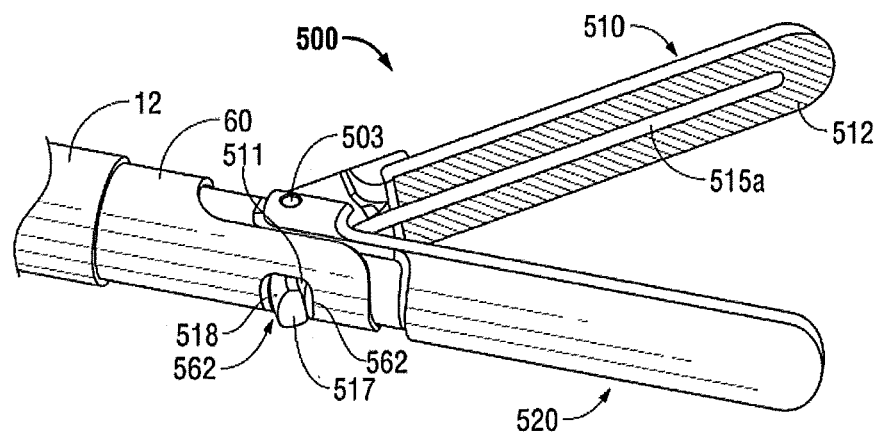
FIG. 53 is an enlarged, perspective view of the end effector assembly with the jaw members shown in open configuration.

The jaw member 510 includes a pivot flange 518 that includes protrusion 517, as best seen in FIG. 53. The protrusion 517 extends from pivot flange 518 and includes an arcuately-shaped inner surface 511 dimensioned to matingly engage the aperture 562 of sleeve 60 upon retraction thereof. Pivot flange 518 also includes a pin slot 519 that is dimensioned to engage pivot pin 503 to allow jaw member 510 to rotate relative to jaw member 520 upon retraction of the reciprocating sleeve 60.

The pivoting jaw member 510 is actuated by sliding the sleeve 60 axially within the shaft 12 such that a distal end 563 of the aperture 562 abuts against the protrusion 517 on the pivoting jaw member 510. Pulling the sleeve 60 proximally closes the jaw members 510 and 520 and pushing the sleeve 60 distally opens the jaw members 510 and 520 for grasping purposes. It is envisioned that grasping, especially for large vessels, may be improved by increasing the relative distance between the seal plate 512 and the pivot 503.

In an embodiment, shown in FIG. 53, the movable jaw member 510 has a seal plate 512 having a texturized surface, e.g., a cross hatch pattern or any suitable type of texturized surface or pattern. The surface 522 of the stationary jaw member 520 may also have a texturized surface. A texturized surface will improve the overall grasping and retaining effectiveness of the effector assembly 500, especially with respect to large vessels and will therefore improve seal performance. The overall flexibility of at least one of the jaw members may be reduced to further improve seal performance.

A knife channel 515*a* and 515*b* runs through the center of jaw members 510 and 520, respectively, such that a blade 585 can cut tissue grasped between the jaw members 510 and 520 when the jaw members 510 and 520 are in a closed position.

The pivoting jaw member 510 interferes with the blade 585 when the pivoting jaw member 510 is open. The blade 585 may be deployed below a threshold angle of the pivoting jaw member 510 to the stationary jaw member 520. Additionally, the length of the blade 585 may be adjusted to control blade deployment.

Figure 50:
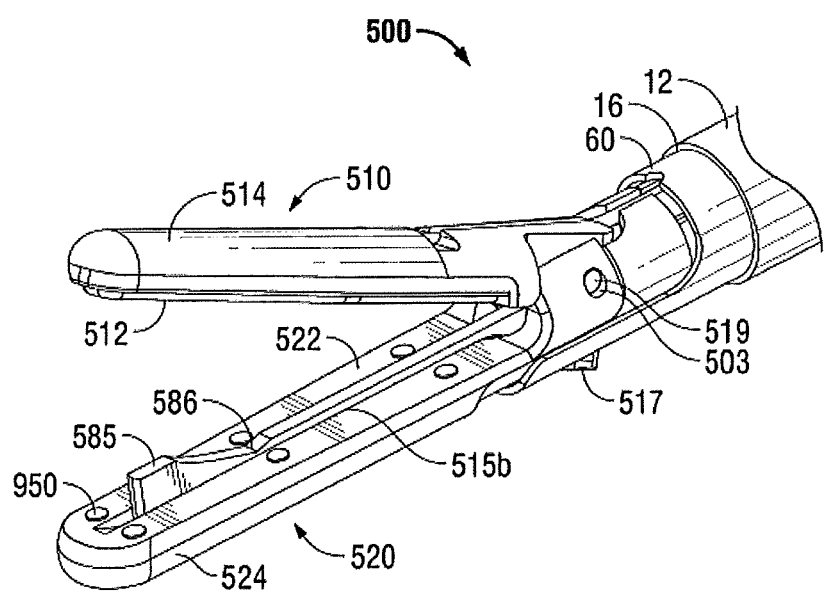
FIG. 50 is an enlarged, perspective view of the end effector assembly with the jaw members shown in open configuration.
Figure 51A:
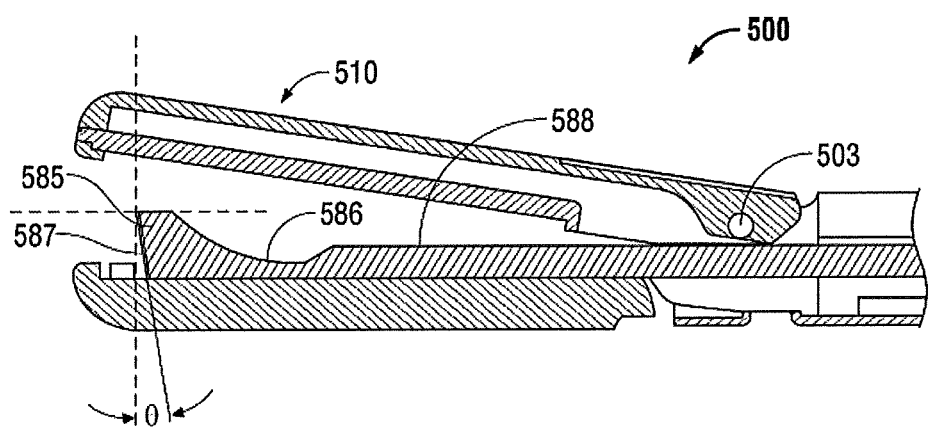
FIG. 51a is an axial cross section of the end effector assembly.
Figure 51B:
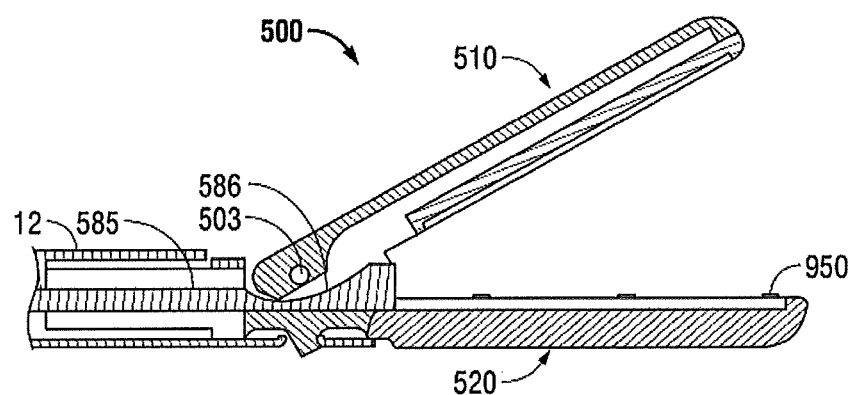
FIG. 51b is an axial cross section of the end effector assembly, illustrating a passive locking mechanism.
Figure 52:
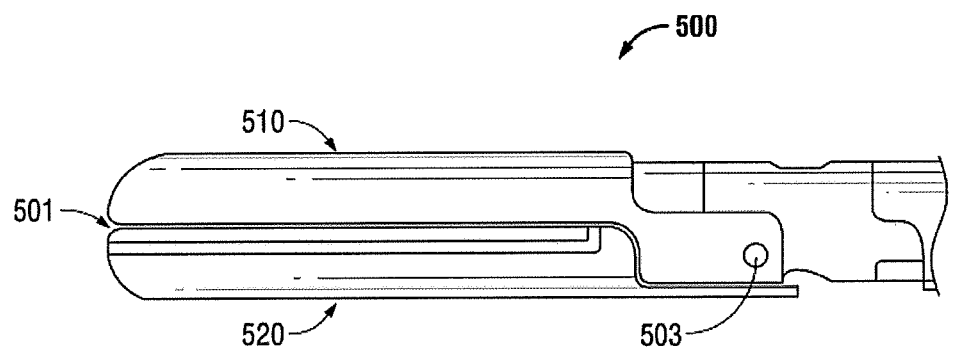
FIG. 52 is an enlarged, side view of the indicated area of the end effector assembly in closed configuration.

A passive safety mechanism is shown in FIG. 51*b*. In an embodiment, when the blade 585 is retracted within the end effector assembly 500, while the jaw members 510, 520 are in an open configuration, a notch 586 defined within the knife blade 585 engages a proximal edge of the end effector assembly, thereby impeding the motion of the knife 585 by preventing distal translation along the knife channel 515*b* (FIG. 50) within the end effector assembly 500.

As shown in FIGS. 52-55, the distal end 501 of the end effector assembly 500 may be blunted. It is envisioned that this will allow the knife channels 515*a* and 515*b* to be within 1 millimeter of an active seal surface. In an embodiment, the knife channels 515*a* and 515*b* are relatively wide to reduce the likelihood of damage to the blade 585 as the jaw members 510 and 520 close upon firing the blade 585.

Knife blade 585 may be a solid blade of unitary construction. Manufacturing the knife blade 585 as a solid blade improves the overall blade strength and makes the knife blade 585 easier to manufacture. Since a solid blade is more durable, it is less likely to break when used.

In an embodiment, a notch 586 is defined along the knife blade 585. A notch 586 is configured to improve the cutting performance of the knife blade 585 during translation thereof. The knife blade 585 may include a shaft 588 having a notch 586 defined therein and a distal end 587, the distal end 587 including a height that is higher than the height of the shaft 588, as shown in FIG. 51*a*. This provides a more robust knife profile for severing tissue. Moreover, the notch 586 may be configured to cooperate with the above-described passive safety lock. More particularly, the proximal edge of the notch 586 may be configured to abut the pivoting jaw member 510 when the jaw members 510, 520 are disposed in an open configuration.

As shown in FIG. 51*a*, the distal end 587 of the blade 585 may have a rake angle θ equal to the angle defined by the distal end 587 of the blade 585 and a perpendicular line to a surface to be cut. The rake angle θ may be positive, as shown in FIG. 51*a*, or may be negative, neutral, or any shape that improves cutting.

Jaw member 520 may also include a series of stop members 950 disposed on the inner facing surfaces of the electrically conductive sealing surface 522 to facilitate gripping and manipulation of tissue and to create a gap when jaw member 510 and jaw member 520 are in a closed position. A series of stop members 950 may be employed on one or both jaw members 510 and 520 depending upon a particular purpose or to achieve a desired result. A detailed discussion of these and other envisioned stop members 950 as well as various manufacturing and assembling processes for attaching and/or affixing the stop members 950 to the electrically conductive sealing surfaces 512, 522 are described in commonly-assigned, co-pending U.S. Application Serial No. PCT/US01/11413 entitled "VESSEL SEALER AND DIVIDER WITH NON-CONDUCTIVE STOP MEMBERS" by Dycus et al.

Figure 54:
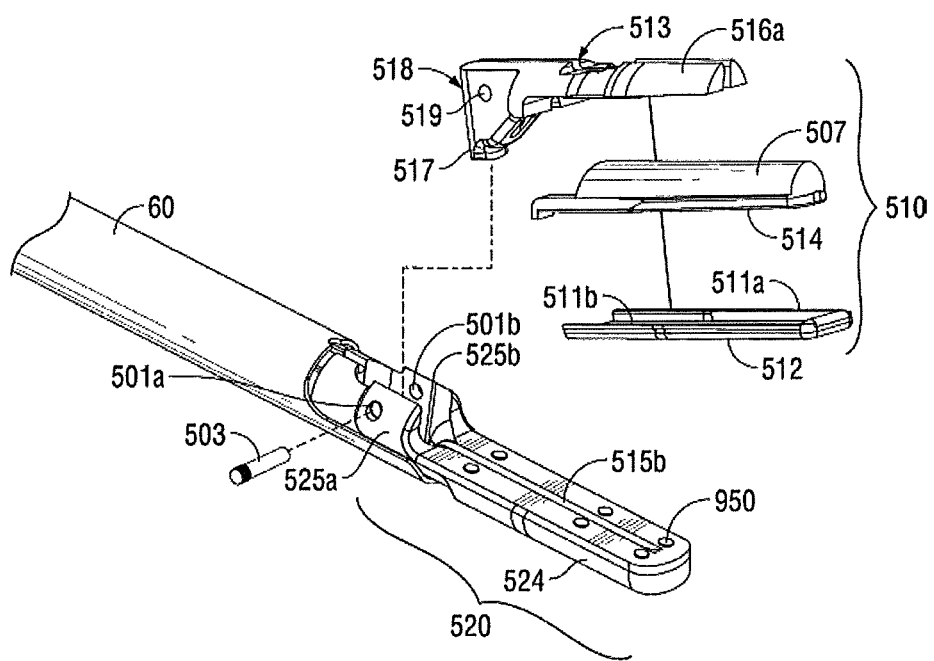
FIG. 54 is an enlarged, top, perspective view of the end effector assembly with parts separated.

Jaw member 510 also includes an insulator 514 and an electrically conductive surface 512. In one embodiment, insulator 514 is dimensioned to securely engage the electrically conductive sealing surface 512. This may be accomplished by stamping, by overmolding a stamped electrically conductive sealing plate and/or by overmolding a metal injection molded seal plate. For example, as shown in FIG. 54, an electrically conductive sealing plate 512 includes a series of upwardly extending flanges 511*a* and 511*b* which are designed to matingly engage the insulator 514. The insulator 514 includes a shoe-like interface 507 disposed at a distal end thereof which is dimensioned to engage the outer periphery 516a of the housing 516 in a slip-fit manner. The shoe-like interface 507 may also be overmolded about the outer periphery of the jaw 510 during a manufacturing step.

As shown in the exploded view of FIG. 54, jaw members 510 and 520 are pivotably mounted with respect to one another such that jaw member 510 pivots in a unilateral fashion from a first open position to a second closed position. More particularly, fixed jaw member, fixed jaw member 520 includes a pair of proximal, upwardly extending flanges 525a and 525b which define a cavity 521 dimensioned to receive flange 518 of movable jaw member 510 therein. Each of the flanges 525a and 525b includes an aperture 501a and 501b, respectively, defined therethrough which secures pivot pin 503 on opposite sides of pivot mount 519 disposed within jaw member 510. As explained in detail below with respect to the operation of the jaw members 510 and 520, proximal movement of the tube 60 engages detent 517 to pivot jaw member 510 to a closed position.

In an embodiment, the tip 511 of the moving jaw 510 is strengthened and stiffened, e.g., with steel to reduce the overall flexibility of the movable jaw member 510 and improve seal performance.

Jaw member 520 includes similar elements to jaw member 510 such as an insulator 524 and an electrically conductive sealing surface 522 that is dimensioned to securely engage the insulator 524. Likewise, the electrically conductive surface 522 and the insulator 524, when assembled, include a longitudinally-oriented channel 515a defined therethrough for reciprocation of the knife blade 585.

When the jaw members 510 and 520 are closed about a tissue, knife channels 515a and 515b form a complete knife channel 515 to allow longitudinal extension of the knife blade 585 in a distal fashion to sever tissue. Knife channel 515 may be completely disposed in one of the two jaw members, e.g., the fixed jaw member 520, depending upon a particular purpose to receive the knife blade 585. Fixed jaw member 520 may be assembled in a similar manner as described above with respect to jaw member 510. The distal end of the knife blade 585 may be dimensioned to ride within the knife channel 515a of the movable jaw 510.

All of these manufacturing techniques produce jaw member 510 having an electrically conductive surface 512 that is substantially surrounded by an insulating substrate 514. The insulator 514, electrically conductive sealing surface 512 and the outer, non-conductive jaw housing 516 can be dimensioned to limit and/or reduce many of the known undesirable effects related to tissue sealing, e.g., flashover, thermal spread and stray current dissipation. Alternatively, it is also envisioned that the jaw members 510 and 520 may be manufactured from a ceramic material and the electrically conductive surface(s) 512 are coated onto the ceramic-like jaw members 510 and 520.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100, 500 relative to the elongated shaft 12.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120 or alternatively 510 and 520. The sensor or feedback mechanism may also measure the impedance across the tissue during sealing and provide an indicator (visual and/or audible) that an effective seal has been created between the jaw members 110 and 120 or alternatively 510 and 520. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003, now issued U.S. Pat. No. 7,137,980.

Moreover, it is contemplated that the trigger assembly 70 may include other types of recoil mechanisms which are designed to accomplish the same purpose, e.g., gas-actuated recoil, electrically-actuated recoil (i.e., solenoid), etc. It is also envisioned that the forceps 10 may be used to cut tissue 420 without sealing. Alternatively, the knife assembly 70 may be coupled to the same or alternate electrosurgical energy source to facilitate cutting of the tissue 420.

Although the figures depict the forceps 10 manipulating an isolated vessel 420, it is contemplated that the forceps 10 may be used with non-isolated vessels as well. Other cutting mechanisms are also contemplated to cut tissue 420 along the ideal tissue plane.

It is envisioned that the outer surface of the end effector assembly 100, 500 may include a nickel-based material, coating, stamping, metal injection molding which is designed to reduce adhesion between the jaw members 110 and 120, and between 510 and 520, with the surrounding tissue during activation and sealing. Moreover, it is also contemplated that the conductive surfaces 112 and 122 of the jaw members 110 and 120, or alternatively the conductive surfaces 512 and 522 of the jaw members 510 and 520, may be manufactured from one (or a combination of one or more) of the following materials: nickel-chrome, chromium nitride, MedCoat 2000 manufactured by The Electrolizing Corporation of OHIO, inconel 600 and tin-nickel. The tissue conductive surfaces 112 and 122, and 512 and 522, may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122, and 512 and 522, made from or coated with Ni200, Ni201 (~100% Ni) also showed improved non-stick performance over typical bipolar stainless steel electrodes.

As can be appreciated, locating the switch 200 on the forceps 10 has many advantages. For example, the switch 200 reduces the amount of electrical cable in the operating room and eliminates the possibility of activating the wrong instrument during a surgical procedure due to "line-of-sight" activation. Moreover, decommissioning the switch 200 when the trigger is actuated eliminates unintentionally activating the device during the cutting process. It is also envisioned that the switch 200 may be disposed on another part of the forceps 10, e.g., the fixed handle 40, rotating assembly 80, housing 20, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A bipolar forceps, comprising:
   a housing;
   a shaft extending from the housing;
   an end effector assembly engaged at a distal end of the shaft, the end effector assembly including two jaw members, at least one of the jaw members movable relative to the other from a first position wherein the jaw members are disposed in spaced relation relative to one another to at least a second position wherein the jaw members are closer to one another and cooperate to grasp tissue therebetween, each of the jaw members including an electrically-conductive sealing surface, and each of the jaw members adapted to connect to an electrosurgical energy source such that the electrically-conductive sealing surfaces are capable of conducting energy through tissue grasped between the jaw members to effect a tissue seal;
   a knife channel defined through at least one of the jaw members, the knife channel having proximal and distal ends; and
   a knife blade slidable through the knife channel from the proximal end to the distal end to sever tissue, the knife blade including a knife shaft having a notch defining a proximal edge, the knife blade defining a distal end having a height that is greater than a height of the shaft, wherein the proximal edge of the notch is adapted to engage a proximal edge of one of the jaw members to block distal translation of the knife blade when the knife blade is in a retracted position and the jaw members are disposed in the first position.

2. The bipolar forceps according to claim 1, wherein the two jaw members include one movable jaw member and one stationary jaw member.

3. The bipolar forceps according to claim 1, wherein at least one of the jaw members is substantially rigid.

4. The bipolar forceps according to claim 1, wherein at least one of the jaw members includes a texturized surface for facilitating grasping and retaining tissue.

5. The bipolar forceps according to claim 1, wherein at least one of the jaw members is substantially insulated.

6. The bipolar forceps according to claim 1, wherein at least one of the jaw member includes a stop member adapted to create a gap between the jaw members when the jaw members are disposed in the second position.

7. The bipolar forceps according to claim 1, wherein the knife blade is a solid blade of unitary construction.

8. The bipolar forceps according to claim 1, wherein the end effector assembly includes one movable jaw member and one stationary jaw member and the knife channel is defined within the movable jaw.

9. The bipolar forceps according to claim 1, wherein an angle is defined by the distal end of the knife blade and a perpendicular line to a surface to be cut and is selected from the group consisting of positive, negative, and neutral angles.

* * * * *